(12) United States Patent
Parry et al.

(10) Patent No.: US 12,083,023 B2
(45) Date of Patent: Sep. 10, 2024

(54) POROUS IMPLANTABLE INTERBODY DEVICES

(71) Applicant: SILONY SPINE CORP, Doral, FL (US)

(72) Inventors: John Parry, West Chester, PA (US); Andrew McQuaide, Lincoln University, PA (US); Kevin Tapper, West Chester, PA (US)

(73) Assignee: SILONY SPINE CORP., Doral, FL (US)

( * ) Notice: Subject to any disclaimer, the term of this patent is extended or adjusted under 35 U.S.C. 154(b) by 0 days.

(21) Appl. No.: 16/165,934

(22) Filed: Oct. 19, 2018

(65) Prior Publication Data

US 2019/0117410 A1     Apr. 25, 2019

Related U.S. Application Data

(60) Provisional application No. 62/575,071, filed on Oct. 20, 2017.

(51) Int. Cl.
*A61F 2/44* (2006.01)
*A61F 2/00* (2006.01)
(Continued)

(52) U.S. Cl.
CPC .......... *A61F 2/4455* (2013.01); *A61F 2/0077* (2013.01); *A61F 2/30767* (2013.01);
(Continued)

(58) Field of Classification Search
CPC .. A61F 2/4455; A61F 2/0077; A61F 2/30767; A61F 2/442; A61F 2/447; A61F 2002/30011; A61F 2002/30013; A61F 2002/30028; A61F 2002/30266; A61F 2002/30787; A61F 2002/3092; A61F 2002/3093; A61F 2002/30985;
(Continued)

(56) References Cited

U.S. PATENT DOCUMENTS

| 5,041,114 A * | 8/1991 | Chapman | A61B 17/744 606/291 |
| 6,045,579 A * | 4/2000 | Hochshuler | A61F 2/4455 606/247 |

(Continued)

FOREIGN PATENT DOCUMENTS

| KR | 100972397 B1 | 7/2010 |
| WO | 2017106780 A1 | 6/2017 |

OTHER PUBLICATIONS

International Search Report and Written Opinion for PCT/US2018/056782 mailed Jan. 11, 2019.
(Continued)

*Primary Examiner* — Zade Coley
*Assistant Examiner* — Diana Jones
(74) *Attorney, Agent, or Firm* — Farber LLC

(57) ABSTRACT

Various porous implantable interbody or spinal fusion devices, which may be formed of metal, metal alloy or polymer are provided. These porous implantable interbody devices may be engineered to have a porous network or scaffold structure for repairing and/or replacing damaged bone segments in the spine while allowing better fusion for improved bone healing and bone regrowth.

16 Claims, 22 Drawing Sheets

(51) Int. Cl.
  *A61F 2/30* (2006.01)
  *A61F 2/46* (2006.01)

(52) U.S. Cl.
  CPC .............. *A61F 2/442* (2013.01); *A61F 2/447* (2013.01); *A61F 2002/30011* (2013.01); *A61F 2002/30028* (2013.01); *A61F 2002/30266* (2013.01); *A61F 2002/30593* (2013.01); *A61F 2002/30787* (2013.01); *A61F 2002/3092* (2013.01); *A61F 2002/3093* (2013.01); *A61F 2002/30985* (2013.01); *A61F 2002/4629* (2013.01); *A61F 2250/0023* (2013.01)

(58) Field of Classification Search
  CPC ...... A61F 2002/4475; A61F 2002/4629; A61F 2250/0023
  See application file for complete search history.

(56) References Cited

U.S. PATENT DOCUMENTS

| | | | |
|---|---|---|---|
| 6,224,631 B1* | 5/2001 | Kohrs | A61F 2/446 623/17.11 |
| 6,942,698 B1 | 9/2005 | Jackson | |
| 2004/0186571 A1* | 9/2004 | Brau | A61F 2/446 623/17.11 |
| 2005/0228500 A1* | 10/2005 | Kim | A61F 2/4611 623/17.13 |
| 2006/0147332 A1 | 7/2006 | Jones et al. | |
| 2007/0142914 A1* | 6/2007 | Jones | A61F 2/30907 623/14.13 |
| 2011/0166656 A1* | 7/2011 | Thalgott | A61F 2/4465 623/17.16 |
| 2012/0191200 A1* | 7/2012 | Choren | A61F 2/3094 623/18.11 |
| 2014/0025181 A1* | 1/2014 | Vanasse | B33Y 50/00 219/76.1 |
| 2014/0288655 A1 | 9/2014 | Parry et al. | |
| 2015/0018956 A1 | 1/2015 | Steinmann et al. | |
| 2015/0073556 A1* | 3/2015 | Liu | A61F 2/447 623/17.16 |
| 2015/0081027 A1 | 3/2015 | Thalgott et al. | |
| 2016/0022431 A1* | 1/2016 | Wickham | A61F 2/447 623/17.16 |
| 2016/0199193 A1* | 7/2016 | Willis | B22F 3/24 623/17.16 |
| 2016/0206442 A1* | 7/2016 | Dvorak | A61F 2/4611 |
| 2016/0287404 A1 | 10/2016 | Hunt et al. | |
| 2016/0296343 A1 | 10/2016 | Bost et al. | |
| 2017/0156878 A1 | 6/2017 | Tsai et al. | |
| 2017/0216036 A1* | 8/2017 | Cordaro | A61F 2/30942 |
| 2017/0239064 A1 | 8/2017 | Cordaro | |
| 2017/0348114 A1* | 12/2017 | Jones | A61F 2/4455 |
| 2017/0367841 A1* | 12/2017 | Wecker | A61F 2/30767 |
| 2019/0099515 A1* | 4/2019 | Bagga | A61L 27/56 |

OTHER PUBLICATIONS

International Preliminary Report on Patentability for corresponding PCT/US2018/056782 mailed Apr. 30, 2020.
Extended European Search Report for corresponding EP Appl. No. 18867971.6 dated Jun. 25, 2021.
Office Action for corresponding Brazilian Appl. No. BR112020007853-0.
Office Action for corresponding Israeli Appl. No. IL273977 dated Dec. 18, 2022.

* cited by examiner

POROUS IMPLANTABLE INTERBODY DEVICES

CROSS-REFERENCE TO RELATED APPLICATIONS

This application claims benefit of U.S. Provisional Application No. 62/575,071, filed Oct. 20, 2017, the entire contents of which are incorporated herein by reference.

TECHNICAL FIELD

The present disclosure relates to orthopedic implants, and more particularly, to spinal implants that facilitate fusion of bone segments. Even more particularly, the disclosure relates to porous implantable interbody devices having an engineered porous scaffold structure for enhanced bone fusion.

BACKGROUND

The integrity of the spine and its subcomponents like the vertebral bodies and intervertebral discs, both of which are well known structural body parts that make up the spine, is a key factor to maintaining a patient's good health. These parts may become weakened, damaged or broken as a result of trauma, injury, or disease (e.g., by tumor, autoimmune disease), or as a result of wear over time, or degeneration caused by the normal aging process.

In many instances, one or more damaged structural body parts can be repaired or replaced with a prosthesis or implant. For example, specific to the spine, one known method of repair is to remove the damaged vertebra (in whole or in part) and/or the damaged disc (in whole or in part) and replace it with an implant or prosthesis. In some cases, it is necessary to stabilize a weakened or damaged spinal region by reducing or inhibiting mobility in the area to avoid further progression of the damage and/or to reduce or alleviate pain caused by the damage or injury. In other cases, it is desirable to join together the damaged vertebrae and/or induce healing of the vertebrae. Fusion of the spine is a well-known and widely practiced medical procedure to alleviate symptoms and potential problems related to spinal instability such as severe back and/or neck pain due to misaligned, damaged or otherwise diseased spines. Accordingly, an implant or prosthesis for rigid fixation of the vertebrae may be utilized to facilitate fusion between two adjacent vertebrae. The implant or prosthesis may be implanted without attachment means, or fastened in position between adjacent structural body parts (e.g., adjacent vertebral bodies).

Typically, an implant or prosthesis is secured directly to a bone structure by mechanical or biological means. One manner of spine repair involves attaching a fusion implant or prosthesis to adjacent vertebral bodies using a fixation element, such as a bone screw. Most implants and their attachment means are configured to provide an immediate, rigid fixation of the implant to the implantation site. Unfortunately, after implantation the implants tend to subside, or settle, into the surrounding environment as the patient's weight is exerted upon the implant. In some cases, this subsidence may cause the rigidly fixed attachment means to either loosen, dislodge or potentially damage one or more of the vertebral bodies.

Several known surgical techniques can be used to implant a spinal prosthesis. The suitability of any particular technique may depend upon the amount of surgical access available at the implant site. For instance, a surgeon may elect a particular entry pathway depending on the size of the patient or the condition of the patient's spine, such as where a tumor, scar tissue, great vessels, or other obstacle is present. Other times, it may be desirable to minimize intrusion into the patient's musculature and associated ligamentous tissue. In some patients who have had prior surgeries, implants or fixation elements may have already been inserted into the patient's spine, and as such, an implant introduction pathway may have to account for these prior existing conditions.

It is well recognized now that porosity, pore size, and pore size distribution all serve important roles in promoting revascularization, bone healing and bone remodeling, and are key contributing factors to successful bone fusion. Further, recent advances in manufacturing techniques now enable intricate porous structures to be easily created from metal, metal alloy or polymer. Some of these techniques include selective layer melting (SLM), E-beam or 3D printing of metal, metal alloy or polymer to create complex metal structures in a layer-by-layer deposition process. These porous metal structures can act as trabecular bone type frameworks for the implantable devices.

Thus, it is desirable to provide porous metallic, metallic alloy or polymeric implantable spinal fusion devices that can repair and/or replace damaged bone segments in the spine while allowing better fusion for improved bone healing and bone regrowth.

BRIEF SUMMARY

The embodiments provide porous implantable interbody or spinal fusion devices formed of metal, metal alloy or polymer. These porous implantable interbody devices may be engineered to have a porous scaffold structure for enhanced bone fusion.

According to one aspect of the present disclosure, an implantable device that is configured for insertion into a patient's intervertebral disc space is provided. In accordance with one exemplary embodiment, the implantable device has a body configured for lateral insertion between vertebral bodies of a spine. The body may have an upper surface, a lower surface, a pair of sidewalls extending in parallel between the upper and lower surfaces, an anterior portion, and a posterior portion tapering from the upper and lower surfaces to form a curved leading edge extending between the sidewalls, the curved leading edge converging at a sharpened tip to allow concomitant distraction of soft tissue during insertion.

At least one of the upper surface, lower surface or sidewalls may further have a porous structure integrated therein, the porous structure being configured to allow bony ongrowth and bony ingrowth therethrough. This porous structure may be integrated into the device such that the interface between the porous structure and the upper surface, lower surface or sidewalls is seamless and void of mechanical or chemical bonding. In addition, the device may further include a central opening between the upper and lower surfaces to receive bone graft material. In some embodiments, the outer surfaces may be roughened or textured.

The porous structure may comprise a mesh or lattice structure, and may be contained within a solid perimeter structure. The porous structure may comprise a plurality of randomized cell units. Each of the cell units may have a dodecahedron, or partial dodecahedron, geometry. The upper and lower surfaces may be non-parallel such that one of the pair of sidewalls has a greater height than the other sidewall to form a wedge-shaped body. The device may include a graft containment porous groove around the central opening.

In one embodiment, the anterior portion of the device may include one or more apertures for receiving a fixation element. The one or more apertures may be hourglass shaped. In another embodiment, the anterior portion of the device may include an aperture for receiving an insertion tool.

The device may be formed of a biocompatible metal, metal alloy, or polymer, and may be 3D printed or manufactured by SLM techniques.

According to another aspect of the present disclosure, an implantable device that is configured for midline insertion into a patient's intervertebral disc space is provided. In accordance with another exemplary embodiment, the implantable device has a generally trapezoidal body configured for midline insertion between vertebral bodies of a spine. The body may have an upper surface, a lower surface, an anterior portion, a posterior portion, and a pair of sidewalls extending between the upper and lower surfaces and connecting the posterior and anterior portions. The device may include rounded or curved posterolateral corners.

At least one of the upper surface, lower surface or sidewalls may further have a porous structure integrated therein, the porous structure being configured to allow bony ongrowth and bony ingrowth therethrough. This porous structure may be integrated into the device such that the interface between the porous structure and the upper surface, lower surface or sidewalls is seamless and void of mechanical or chemical bonding. In addition, the device may further include a central opening between the upper and lower surfaces to receive bone graft material. In some embodiments, the outer surfaces may be roughened or textured.

The porous structure may comprise a mesh or lattice structure, and may be contained within a solid perimeter structure. The porous structure may comprise a plurality of randomized cell units. Each of the cell units may have a dodecahedron geometry. The upper and lower surfaces may be non-parallel such that one of the pair of sidewalls has a greater height than the other sidewall to form a wedge-shaped body. The device may include a graft containment porous groove around the central opening.

In one embodiment, the anterior portion of the device may include one or more apertures for receiving a fixation element. The one or more apertures may be hourglass shaped. In another embodiment, the anterior portion of the device may include an aperture for receiving an insertion tool.

The device may be formed of a biocompatible metal, metal alloy or polymer, and may be 3D printed or manufactured by SLM techniques.

In accordance with still another exemplary embodiment, the implantable device may be sized and configured for insertion into the cervical spine. The device may be configured to allow stacking of the devices at different spinal levels.

According to still another aspect of the present disclosure, an implantable device that is configured for a lateral oblique angular insertion into a contra lateral and posterior spinal space is provided. In accordance with one exemplary embodiment, the implantable device has a body with an upper surface, a lower surface, and a pair of sidewalls extending therebetween. The sidewalls may be connected by an intermediate wall segment and converge at a nose or tip. The pair of sidewalls may include one sidewall that is longer than the other sidewall, and form a shark's fin shaped body.

The body may further include a central opening extending through the upper and lower surfaces. The body may be configured for insertion along a trajectory represented by an axis that is oblique relative to a midline of a vertebral body of a patient's spine.

The implantable device facilitates fusion and may be used with a graft material that can be placed within the central opening. At least one of the upper surface, lower surface or sidewalls may further have a porous structure integrated therein, the porous structure being configured to allow bony ongrowth and bony ingrowth therethrough. This porous structure may be integrated into the device such that the interface between the porous structure and the upper surface, lower surface or walls is seamless and void of mechanical or chemical bonding. In addition, the outer surfaces may be roughened or textured.

The porous structure may comprise a mesh or lattice structure, and may be contained within a solid perimeter structure. The porous structure may comprise a plurality of randomized cell units. Each of the cell units may have a dodecahedron, or partial dodecahedron, geometry. The upper and lower surfaces may be non-parallel such that one of the pair of sidewalls has a greater height than the other sidewall to form a wedge-shaped body. The device may include a graft containment porous groove around the central opening.

In one embodiment, the intermediate wall segment may include one or more apertures for receiving a fixation element. The one or more apertures may be hourglass shaped. In another embodiment, the intermediate wall segment may include an aperture for receiving an insertion tool.

The device may be formed of a biocompatible metal, metal alloy or polymer, and may be 3D printed or manufactured by SLM techniques.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 2A-2F show various views of an exemplary embodiment of a porous implantable interbody device of the present disclosure configured for lateral insertion into the spine, in which:

FIG. 2A is a top-down view of the implantable device showing the solid scaffold structure without the porous component;

FIG. 2B is a top-down view of the implantable device of FIG. 2A showing the porous component in combination with the solid scaffold structure;

FIG. 2C is a side view of the implantable device of FIG. 2B;

FIG. 2D is a side view of the implantable device of FIG. 2A;

FIG. 2E is a cross-sectional view of the implantable device of FIG. 2D along lines B-B; and FIG. 2F is a cross-sectional view of the implantable device of FIG. 2A along lines A-A.

FIGS. 3A-3F show various views of another exemplary embodiment of a porous implantable interbody device of the present disclosure configured for lateral insertion into the spine, in which:

FIG. 3A is a top-down view of the implantable device showing the solid scaffold structure without the porous component;

FIG. 3B is a top-down view of the implantable device of FIG. 3A showing the porous component in combination with the solid scaffold structure;

FIG. 3C is a side view of the implantable device of FIG. 3B;

FIG. 3D is a side view of the implantable device of FIG. 2A;

FIG. 3E is a cross-sectional view of the implantable device of FIG. 3D along lines B-B; and FIG. 3F is a cross-sectional view of the implantable device of FIG. 3A along lines A-A.

FIGS. 4 and 5A-5I show various views of an exemplary embodiment of a porous implantable interbody device of the present disclosure configured for midline insertion into the spine, in which:

FIG. 4 is photograph showing a cross-sectional view of the implantable interbody device;

FIG. 5A is a top-down view of the implantable device showing the porous component without the solid scaffold structure;

FIG. 5B is a perspective view of the implantable device of FIG. 5A;

FIG. 5C is a rear view of the implantable device of FIG. 5A;

FIG. 5D is a side view of the implantable device of FIG. 5A;

FIG. 5E is a perspective view of the implantable device of FIG. 5A showing the solid scaffold structure without the porous component;

FIG. 5F is another perspective view of the implantable device of FIG. 5A showing the solid scaffold structure without the porous component;

FIG. 5G is a cross-sectional view of the implantable device of FIG. 5A along lines A-A showing the solid scaffold structure with the porous component;

FIG. 5H is a side view of the implantable device of FIGS. 5E and 5F; and

FIG. 5I is a cross-sectional view of the implantable device of FIG. 5H showing the solid scaffold structure with the porous component.

FIGS. 6A-6I show various views of another exemplary embodiment of a porous implantable interbody device of the present disclosure configured for midline insertion into the spine, in which:

FIG. 6A is a top-down view of the implantable device showing the porous component without the solid scaffold structure;

FIG. 6B is a perspective view of the implantable device of FIG. 6A;

FIG. 6C is a rear view of the implantable device of FIG. 6A;

FIG. 6D is a side view of the implantable device of FIG. 6A;

FIG. 6E is a perspective view of the implantable device of FIG. 6A showing the solid scaffold structure without the porous component;

FIG. 6F is another perspective view of the implantable device of FIG. 6A showing the solid scaffold structure without the porous component;

FIG. 6G is a cross-sectional view of the implantable device of FIG. 6A along lines A-A showing the solid scaffold structure with the porous component;

FIG. 6H is a side view of the implantable device of FIGS. 6E and 6F; and

FIG. 6I is a cross-sectional view of the implantable device of FIG. 6H showing the solid scaffold structure with the porous component.

FIGS. 7A-7H show various views of an exemplary embodiment of a porous implantable interbody device of the present disclosure configured for insertion into the cervical spine, in which:

FIG. 7A is a top-down view of the implantable device showing the porous component without the solid scaffold structure;

FIG. 7B is a perspective view of the implantable device of FIG. 7A;

FIG. 7C is a rear view of the implantable device of FIG. 7A;

FIG. 7D is a side view of the implantable device of FIG. 7A;

FIG. 7E is a perspective view of the implantable device of FIG. 7A showing the solid scaffold structure without the porous component;

FIG. 7F is another perspective view of the implantable device of FIG. 7A showing the solid scaffold structure without the porous component;

FIG. 7G is a cross-sectional view of the implantable device of FIG. 7D along lines A-A showing the solid scaffold structure with the porous component; and FIG. 7H is a cross-sectional view of the implantable device of FIG. 7A showing the solid scaffold structure with the porous component.

FIGS. 8A-8H show various views of another exemplary embodiment of a porous implantable interbody device of the present disclosure configured for insertion into the cervical spine, in which:

FIG. 8A is a top-down view of the implantable device showing the porous component without the solid scaffold structure;

FIG. 8B is a perspective view of the implantable device of FIG. 8A;

FIG. 8C is a rear view of the implantable device of FIG. 8A;

FIG. 8D is a side view of the implantable device of FIG. 8A;

FIG. 8E is a perspective view of the implantable device of FIG. 8A showing the solid scaffold structure without the porous component;

FIG. 8F is another perspective view of the implantable device of FIG. 8A showing the solid scaffold structure without the porous component;

FIG. 8G is a cross-sectional view of the implantable device of FIG. 8D along lines A-A showing the solid scaffold structure with the porous component; and FIG. 8H is a cross-sectional view of the implantable device of FIG. 8A showing the solid scaffold structure with the porous component.

FIGS. 9A-9E show various views of an exemplary embodiment of a porous implantable interbody device of the present disclosure configured for lateral-oblique insertion into the spine, in which:

FIG. 9A is a top-down view of the implantable device showing the solid scaffold structure without the porous component;

FIG. 9B is a cross-sectional view of the implantable device of FIG. 9D along lines A-A with the porous component;

FIG. 9C is a side view of the implantable device of FIG. 9A;

FIG. 9D is another side view of the implantable device of FIG. 9A; and

FIG. 9E is a cross-sectional view of the implantable device of FIG. 9A along lines B-B with the porous component.

FIGS. 10A-10E show various views of another exemplary embodiment of a porous implantable interbody device of the present disclosure configured for lateral-oblique insertion into the spine, in which:

FIG. 10A is a top-down view of the implantable device showing the solid scaffold structure without the porous component;

FIG. 10B is a cross-sectional view of the implantable device of FIG. 10D along lines A-A with the porous component;

FIG. 10C is a side view of the implantable device of FIG. 10A;

FIG. 10D is another side view of the implantable device of FIG. 10A; and

FIG. 10E is a cross-sectional view of the implantable device of FIG. 10A along lines B-B with the porous component.

DETAILED DESCRIPTION

The present disclosure provides various porous implantable interbody or spinal fusion devices, which may be formed of metal, metal alloy or polymer[[,]]. These porous implantable interbody devices may be engineered to have a porous network or scaffold structure for repairing and/or replacing damaged bone segments in the spine while allowing better fusion for improved bone healing and bone regrowth.

Figure 1:
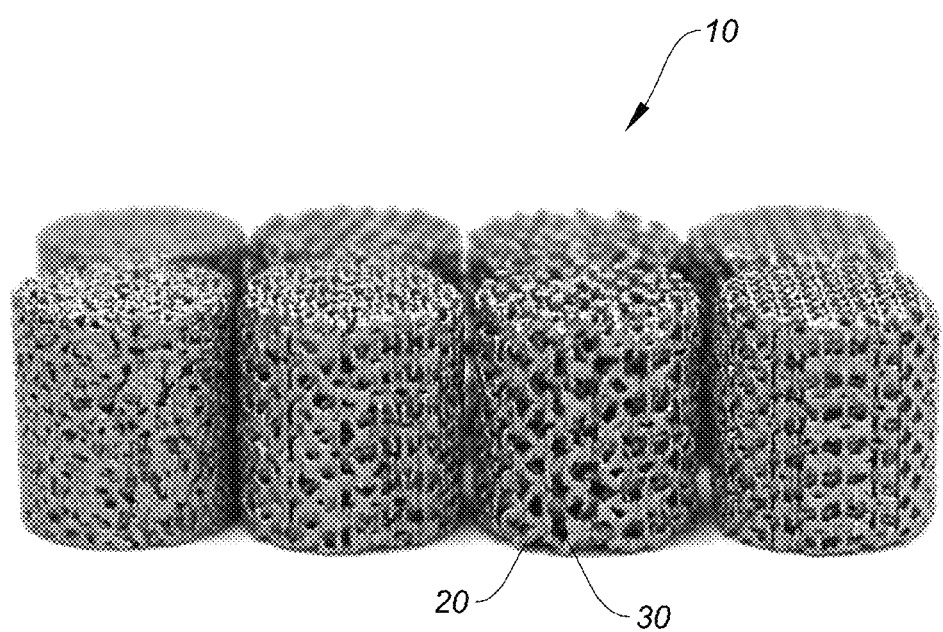
FIG. 1 is a photograph showing various complex porous scaffold structures for forming the porous implantable interbody devices of the present disclosure.

Porosity, pore size, and pore size distribution all play important roles in promoting revascularization, bone healing and bone remodeling, and are key contributing factors to successful bone fusion. With recent advances in manufacturing techniques, it is now possible to create intricate, interlinked or interconnected porous structures such as the various porous lattice structures shown in FIG. 1. Some of these manufacturing techniques include selective layer melting (SLM) or 3D printing of metal, metal alloy or polymer. Both techniques employ a layer-by-layer deposition approach to building these types of complex and interlinked, interconnected porous metal structures. As can be seen in the models of FIG. 1, these porous metal structures 10 can have varying sized pores 30 interspersed throughout as well as solid portions 20, while still being interlinked so as to form a complex open channel configuration extending all the way through.

The manufacturing technique also enables the device to have repetitive, specifically shaped geometric units built to form an interconnected web of repeating geometric units of cells. In one embodiment, the cell unit is a dodecahedron, or partial dodecahedron, for example. The cell unit may be based on a lightweight cell structure that is suitable for natural bone ongrowth and/or bone ingrowth. Thus, the device may include a porous lattice structure that comprises a plurality of dodecahedron shaped cell units. The resultant devices have metal bodies with randomized, organic cell geometry or pore structure geometry and pore size that mimics the structure of natural bone. Accordingly, smaller cell units may nest within larger cell units. These cells may have smooth or roughened, textured surfaces. In this manner, these engineered devices mimic trabecular bone and serve as improved metal frameworks to facilitate better bony fusion for improved bone healing and bone regrowth, as will be described in greater detail below.

Turning now to the drawings, FIGS. 2A to 10E illustrate various porous implantable interbody, or spinal fusion, devices of the present disclosure. These devices may be configured for a specific type of surgical insertion approach into the spine, or for use at a specific spinal segment, while having a common platform of the complex, interconnected porous network described herein. Each device may serve as an engineered porous scaffold for bone fusion. These devices may be formed of a metal, metal alloy or polymer, as well as other, different materials, and can therefore be considered a hybrid titanium alloy support structure with a scaffold designed for ease of use and low stiffness, to minimize risk of stress shielding and promote mechanical stimulus of graft material, in line with Wolff's law.

The devices may be configured to have optimized endplate contact surface area for enhanced subsidence resistance to mitigate risk of subsidence, which has been a historic issue with bulky metallic implants. In one embodiment, the device may be between 50% to 90% porous. The engineered porous scaffold platform may include scaffold based features like variable or random fine pore geometry (such as, for example, pores in the range of about 0.3 to about 0.7 mm, with nominal pores size of about 0.45 mm) that is intended to optimize fusion/healing with rapid new bone formation. The pores are interspersed throughout solid portions of the scaffold, which solid portions provide a smooth surface or appearance, and create a lattice-like, or mesh-like, structure of random porous and non-porous (solid) surfaces, as shown in FIG. 1. Thus, the scaffolds on which the implantable interbody devices of the present disclosure are based have an organic appearance (i.e., mimic natural trabecular bone structure). The devices can be provided in various sizes and configurations, as stated above, for specific clinical applications while providing superior total bone graft volume. For purposes of illustration, certain specifically configured implantable interbody devices of the present disclosure are now described in greater detail below.

Implantable Interbody Devices for Lateral Approach

As shown in FIGS. 2A-2F and 3A-3F, exemplary embodiments of implantable spinal fusion or interbody devices 100, 100' configured for lateral insertion into the spine can be provided in accordance with the principles of the present disclosure.

FIGS. 2A to 2F illustrate an exemplary embodiment of an implantable interbody device 100 that may be implanted in the intervertebral space between vertebral bodies and secured to the vertebral bodies with fixation screws. The implantable interbody device 100 may be employed in the lumbar or thoracic regions.

The implantable interbody device 100 may include posterior and anterior portions 112, 114 and upper and lower surfaces profiled to correspond with the profile of any bone material to which they are to be secured. Upper and lower surfaces 116, 118 may be flat or planar, or may be domed or convexly curved. A pair of sidewalls 120 extends between the upper and lower surfaces 116, 118 and connects to the posterior and anterior portions 112, 114. The implantable interbody device 100 may include a central opening or lumen 124 extending between the upper and lower surfaces 116, 118 to facilitate bony ongrowth and bony ingrowth or fusion between adjacent bone segments, such as vertebral bodies. If so desired, the opening 124 may be used to receive and hold bone graft material to further enhance the bone fusion process.

Figure 2A:
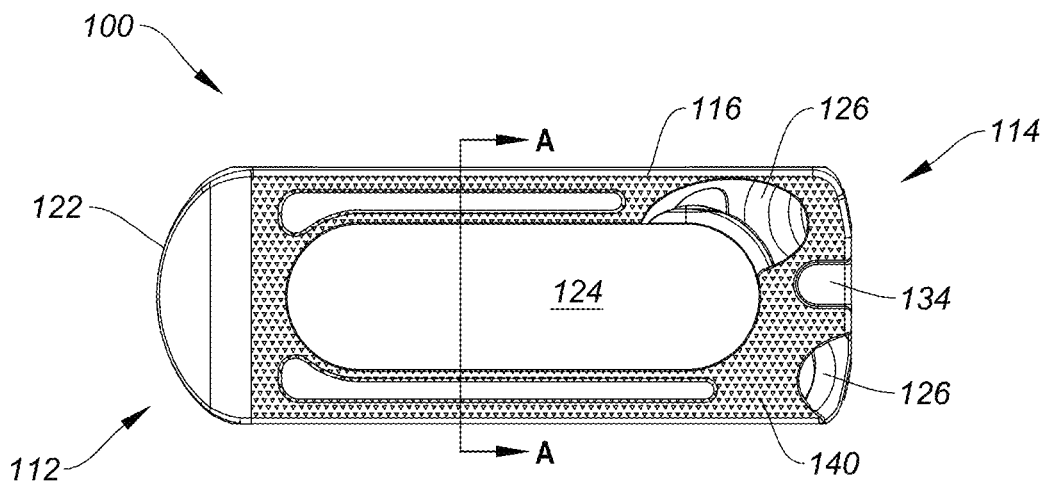
Figure 2B:
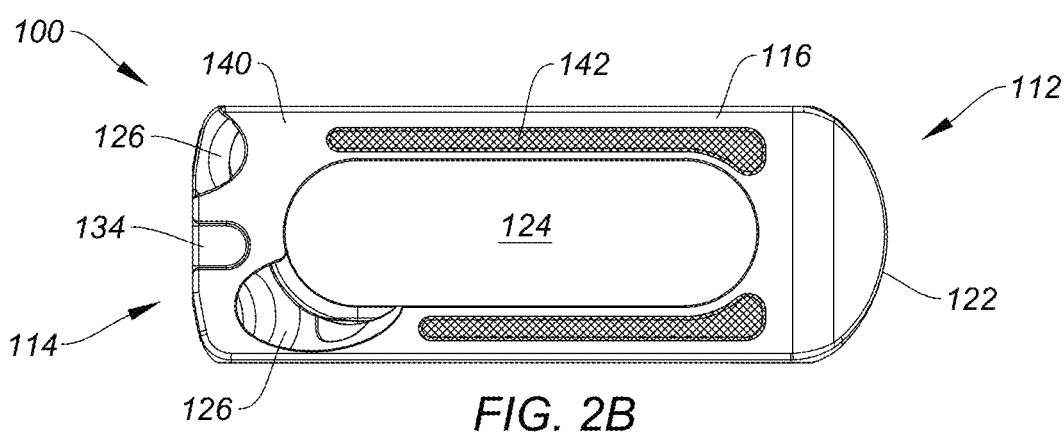
Figure 2C:
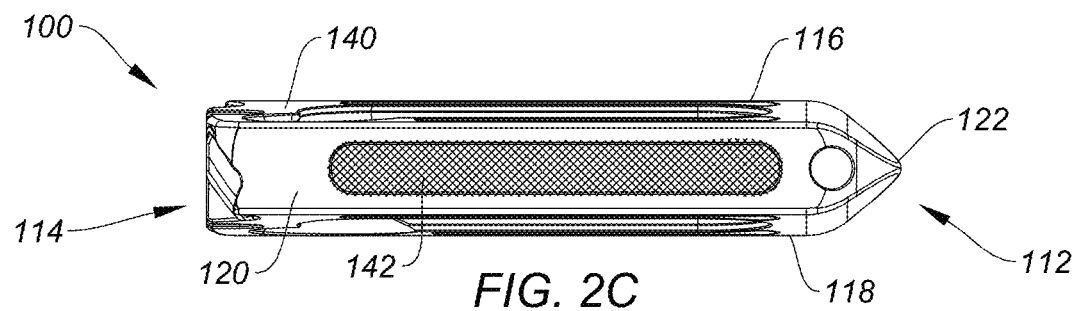

The implantable device 100 shown in FIGS. 2B, 2C, 2E, and 2F include a porous lattice or mesh component 142 that can be incorporated within the solid structural component 140. For instance, as shown in FIG. 2A, the implantable device 100 may have a solid structural component 140 with open spaces that can be filled with the porous component 142, as shown in FIGS. 2B, 2C, 2E and 2F. The combination and resultant device 100 provides a porous component all around the solid structural component 140 such as on the sidewalls 120 and on the top and bottom surfaces 116, 118. The lower surface 118 may include the same type of porous lattice or porous network component 142 integrated therein. Accordingly, the implantable interbody device 100 of FIGS. 2A to 2F incorporates the principles of a network of pores and solid surfaces that is shown in FIG. 1 to create an improved fusion facilitating device 100 not heretofore seen.

Since the porous component is interconnected to the solid component, greater integration is achieved than with conventional textured coatings, titanium spray coatings, or surface rougheniings. These additional enhancements are considered optional now. For example, the solid surfaces of the device 100 may be further coated or provided with surface rougheniings or textured features. As shown in FIG. 2A, the solid scaffold structure 140 may be formed with a surface texture, and may therefore provide an outer surface that is textured, such as a roughened texture or one with discrete geometric protrusions, to enhance surface attachment.

The extensive porous lattice areas 142 that are engineered to extend all the way around the device 100 allow for more interaction with bone than with conventional treatment methods. Such features are possible for metallic, metallic alloy or polymeric devices based on layer-by-layer deposition manufacturing techniques like 3D printing or selective layer melting (SLM) of metal, metal alloy or polymer. And since the entire device 100 may be formed of metal, metal alloy or polymer, no additional visualization markers are necessary for visualization. Because the devices 100 are created in a single process without the need for connecting subcomponents together, one of the key benefits of the devices is that the interface between the porous lattice areas 142 and the upper surface 116, lower surface 118 or sidewalls 120 is seamless and void of mechanical or chemical bonding, adding to the overall strength of the devices 100. For perspective, FIG. 2A illustrates the device 100 with the porous lattice structure 142 removed, leaving the solid part of the device only. Thus, the porous lattice structure 142 is surrounded by a solid perimeter structure for strength. The porous lattice structure 142 can comprise randomized cell/pore size and cell/pore structure or geometry, while the unit cell structure (i.e., the structure of the porous lattice structure 142) is based on a unique lightweight structure such as a dodecahedron. All of these features create a more organic-appearing and behaving environment that is ideal for bone healing and bone growth.

In some embodiments, the sidewalls 120 may be concave to create a unique C- or I-beam shape when viewed in cross-section, which serves to enhance support of the endplates and reduce risk of subsidence, while also being able to promote a lightweight, lower stiffness structure. This unique C- or I-beam cross-sectional shape of the sidewalls also helps to enhance support of any graft material contained within the central opening 124 or of biologics formed to nest within this donut shaped lumen. The sidewalls 120 and lumens together may be radiused in such a way to create a self-supporting arch and other geometries to reduce the need for additional supports during the manufacturing process, such as when 3D printing.

To facilitate ease of insertion, the posterior portion, or leading end 112 may be tapered or otherwise shaped for concomitant distraction of soft tissue during insertion. For example, the posterior portion 112 may be a sharp, bullet shaped nose or tip 122. The unique geometry of the device 100 including this sharpened tip 122 supports reduced insertion forces, and may also help to separate tissue during the insertion. This can be helpful, for example, where scar tissue or other obstructions are present at the implantation site, or where there is stenosis and/or some other anatomic anomaly such as where the endplates have grown together.

Figure 2D:
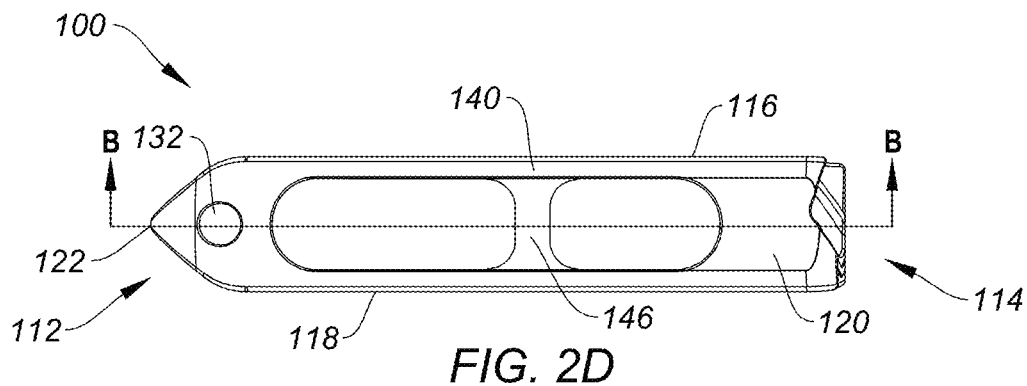
Figure 2E:
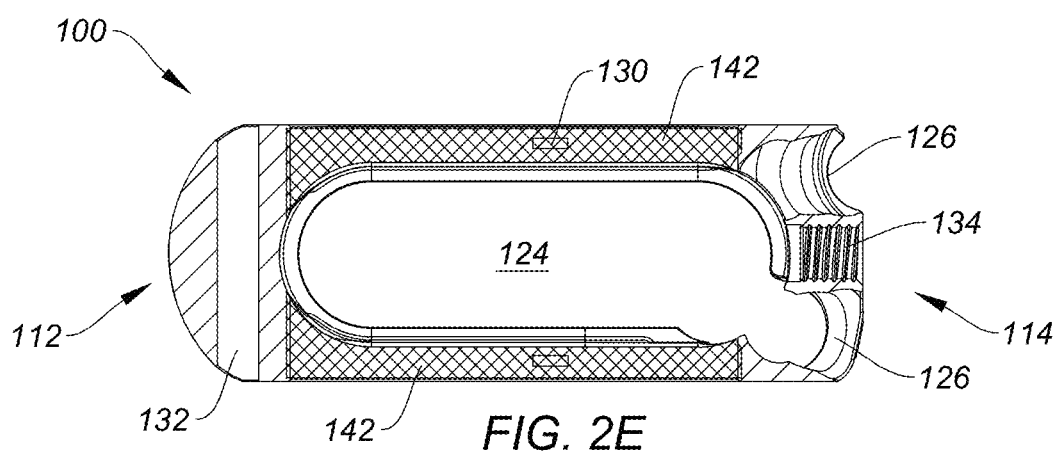

In the embodiment of FIG. 2D, the device 100 may have an indicator nose through hole 132. The indicator nose through hole 132 may be configured for detection and may be used as a visual aid, such as an x-ray indicator. In addition, as shown in FIG. 2E, additional visual aids such as x-ray indicators 130 may be present in the device 100 to assist with the navigation and orientation of the device 100 during implantation. Furthermore, the device 100 may include an "I" beam 146 that may serve as an x-ray marker for assistance with visualization and spatial orientation.

The anterior portion, or trailing end 114 of the implantable interbody device 100 can include holes 126 for receiving fixation elements, such as for example, bone screws, and a hole 134 for receiving an insertion instrument. The hole 134 may be threaded, as shown in FIG. 2E. In the embodiment shown, the implantable interbody device 100 can include two screw holes 126, one extending superiorly and one extending inferiorly. In other embodiments, instead of having one superior angled hole and one inferior angled hole in the device 100 as shown, the implantable device 100 may have two superior angled holes, or may be configured to have two inferior angled holes. One skilled in the art will appreciate that the implantable device 100 may comprise any number of holes at any location on the device 100, or may have no screw holes at all, as shown in the embodiment of FIGS. 3A-3F.

The holes 126 provide a path through which securing means (e.g., fixation elements such as bone screws) may be inserted so as to secure the device 100 to respective superior and inferior vertebral bodies. The holes 126 may be configured to accommodate a variety of securing means, such as screws, pins, staples, or any other suitable fastening device. In one embodiment, the fixation screws may be self-tapping and/or self-drilling and may be of a bone-screw-type, such as those well known to skilled artisans. The screws can be sized and shaped for unicortical or bicortical bone fixation.

Further, in some embodiments, if so desired the holes 126 of the implantable interbody device 100 may be configured to permit a predetermined amount of screw toggle (i.e., angular skew) and enable a lag effect when the fixation screw is inserted and resides inside the hole or lumen 126. In other words, the holes 126 permit a certain degree of nutation by the screw and thus the screws may toggle from one position to one or more different positions, for instance, during subsidence. For instance, holes 126 may be configured with a conical range of motion (i.e., angular clearance)

of about 25 to about 35 degrees, although it is contemplated that an even larger range may be possible such as 20 to 40 degrees, or 15 to 45 degrees. In one embodiment, the range is about 22 to 28 degrees. It is also believed that the predetermined screw toggle (permitted by the clearance between the lumen, or hole 26 and the screw) promotes locking of the screw to the device 100 after subsidence subsequent to implantation. Alternatively, the holes 126 of the device 100 may be configured with little or no clearance to achieve rigid fixation, for example, when the device 100 is to be implanted into sclerotic bone. According to one aspect of the disclosure, in some embodiments, the screw holes may be hourglass shaped so as to facilitate manufacturing by SLM, E-beam or 3D printing. Further, the screw holes 126 may include a screw hole indicator groove, screw hole direction indicator arrow, screw hole direction indicator arrow, a reverse chamfer or overhang feature, countersink, visual response feedback feature, and/or tactile response feedback feature, similar to the screw holes described in U.S. patent application Ser. No. 15/428,601, now U.S. Patent Application Publication No. US2017/0239061 A1, the contents of which are hereby incorporated by reference.

Figure 2F:
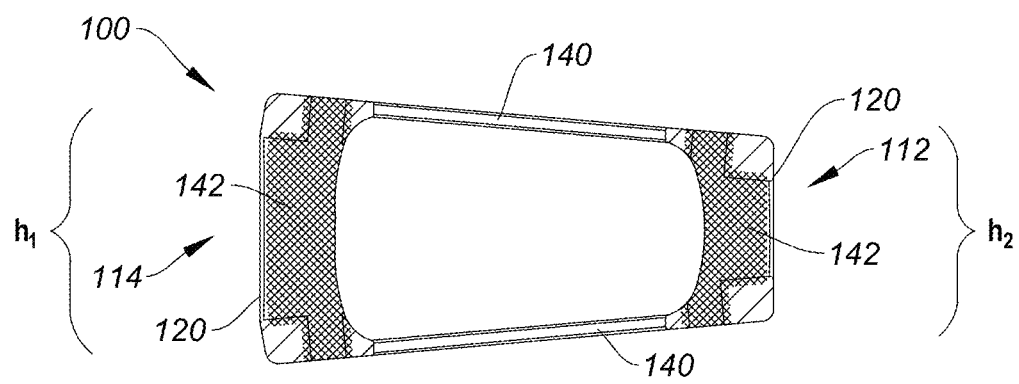

In some embodiments, the implantable interbody device 100 may have non-parallel upper and lower surfaces 116, 118 to form a wedge-shaped body. As shown in FIG. 2F, the device 100 may have a sloped or tapered profile such that one sidewall 120 has a greater height $h_1$ than the height $h_2$ of the opposed sidewall 120. The upper and lower surfaces 116, 118 thus are configured such that they are angled relative to one another. However, one skilled in the art will appreciate that the implantable interbody device 100 may also be provided with parallel upper and lower surfaces 116, 118. The implantable interbody device 100 may have any suitable shape or size to allow it to be used under lordotic or kyphotic conditions. For instance, in one example, the implantable interbody device 100 may have a 12 degree lordotic profile from an anterior-posterior (A-P) view.

FIGS. 3A to 3F illustrate another exemplary embodiment of an implantable interbody device 100' that may be implanted in the intervertebral space between vertebral bodies by a lateral approach, without the need for additional screw fixation. The implantable interbody device 100' shares similar features to the implantable interbody device 100 of FIGS. 2A-2F, with like features having the same reference number followed by the symbol "'" for convenient reference. Like the implantable interbody device 100 previously described, device 100' may also be employed in the lumbar or thoracic regions.

The implantable interbody device 100' may include posterior and anterior portions 112', 114' and upper and lower surfaces 116', 118' profiled to correspond with the profile of any bone material to which they are to be secured. Upper and lower surfaces 116', 118' may be flat or planar, or may be domed or convexly curved. A pair of sidewalls 120' extends between the upper and lower surfaces 116', 118' and connects to the posterior and anterior portions 112', 114'. The implantable interbody device 100' may include a central opening or lumen 124' extending between the upper and lower surfaces 116', 118' to facilitate bony ongrowth and/or bony ingrowth or fusion between adjacent bone segments, such as vertebral bodies. If so desired, the opening 124' may be used to receive and hold bone graft material to further enhance the bone fusion process.

The implantable device 100' shown in FIGS. 3B, 3C, 3E, and 3F may include a porous lattice or mesh component 142' that can be incorporated within the solid structural component 140' similar to implantable device 100 described above.

Figure 3A:
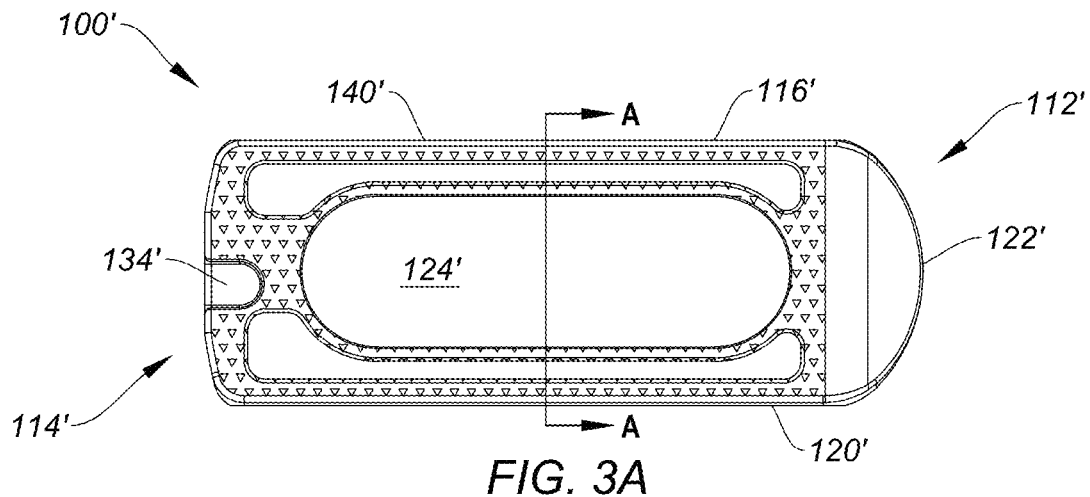
Figure 3B:
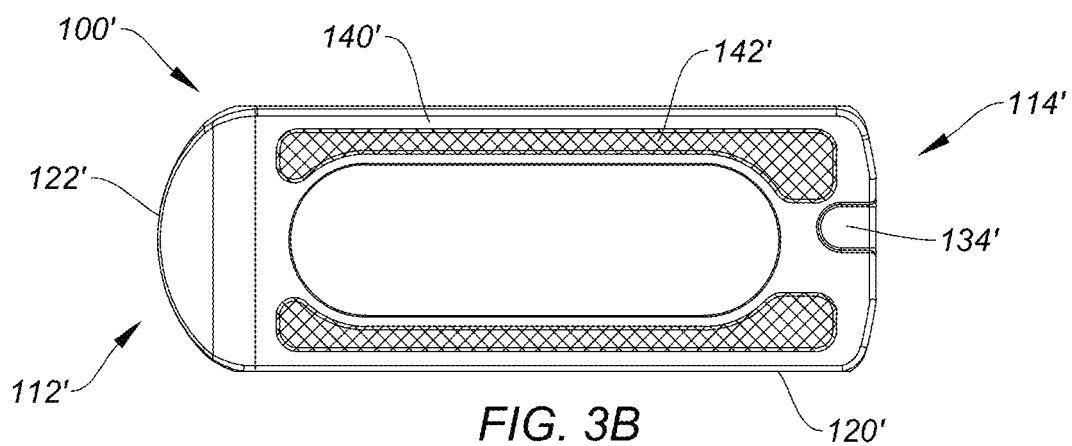
Figure 3C:
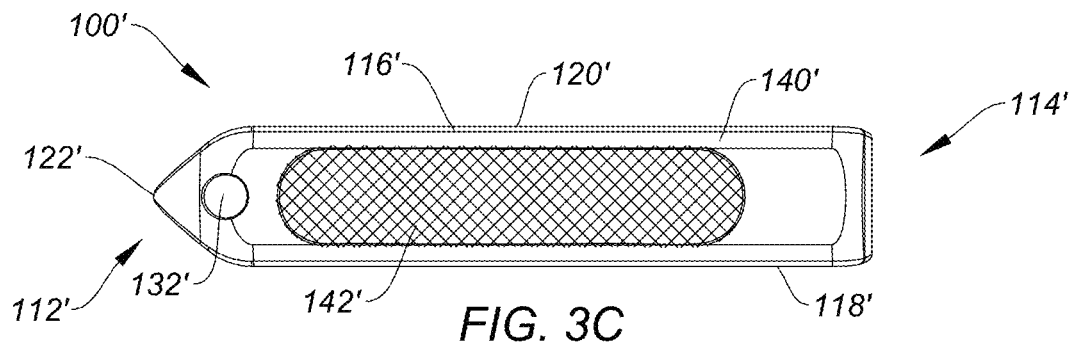
Figure 3D:
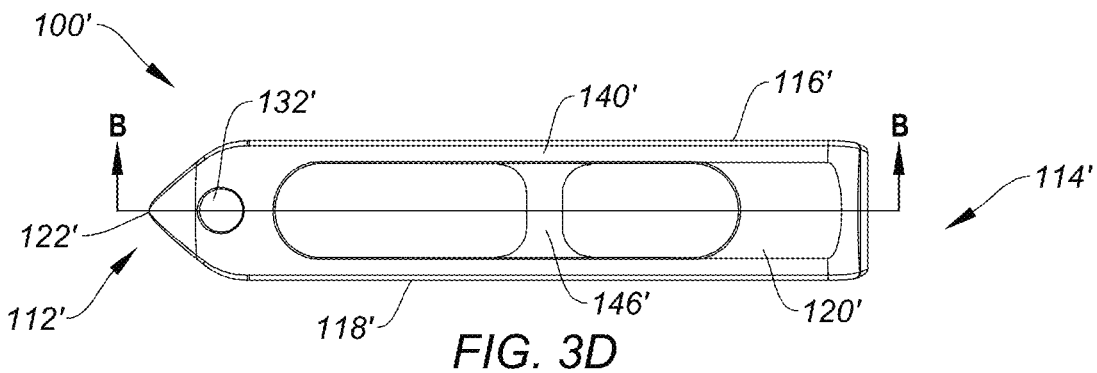
Figure 3E:
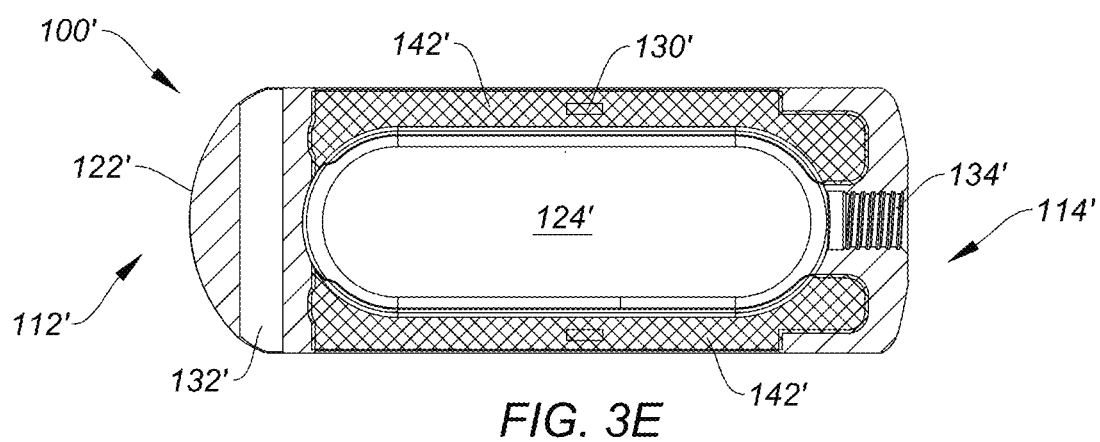
Figure 3F:
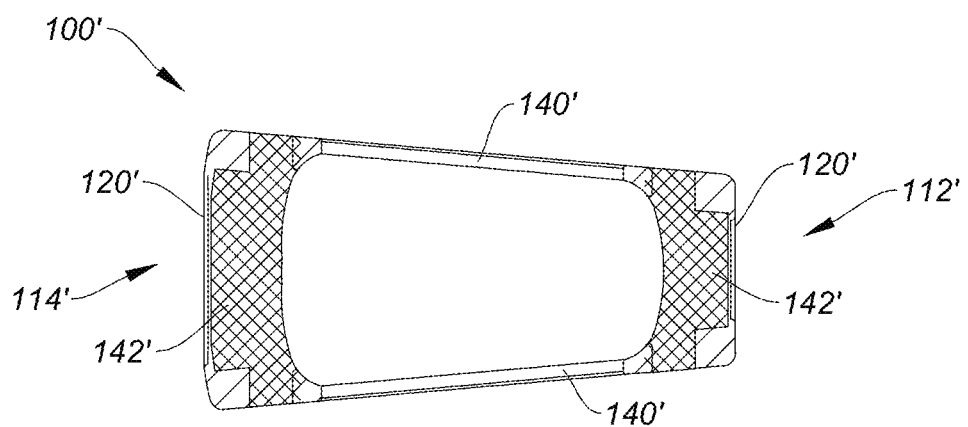

In some embodiments, the sidewalls 120' may be concave to create a unique C- or I-beam shape, and the sidewalls 120' and lumens together may be radiused in such a way to create a self-supporting arch and other geometries to reduce the need for additional supports during the manufacturing process, such as when 3D printing. Like implantable device 100, the posterior portion, or leading end 112' may be tapered or otherwise shaped for concomitant distraction of soft tissue during insertion. For example, the posterior portion 112' may be a sharp, bullet shaped nose or tip 122'. In the embodiment of FIG. 3D, the device 100' may have an indicator nose through hole 132'. The indicator nose through hole 132' may be configured for detection and may be used as a visual aid, such as an x-ray indicator. In addition, as shown in FIG. 3E, additional visual aids 130' such as x-ray indicators may be present in the device 100' to assist with the navigation and orientation of the device 100 during implantation. Furthermore, the device 100' may include an "I" beam 146' that may serve as an x-ray marker for assistance with visualization and spatial orientation.

Unlike implantable device 100, the implantable device 100' of the present embodiment does not include any screw holes at its anterior portion, or trailing end 114'. However, similar to implantable device 100, the implantable device 100' of the present embodiment may include hole 134' for receiving an insertion instrument. The hole 134' may be threaded, as shown in FIG. 3E, similar to the one shown and described above for implantable device 100.

Implantable Interbody Devices for Midline Approach

As shown in FIGS. 4, 5A-5I and 6A-6I, exemplary embodiments of implantable spinal fusion or interbody devices 200, 200' configured for midline insertion into the spine can be provided in accordance with the principles of the present disclosure.

FIGS. 4 and 5A to 5I illustrate an exemplary embodiment of an implantable spinal fusion or implantable interbody device 200 configured for midline insertion into the spine. The implantable device 200 may be implanted in the intervertebral space between vertebral bodies and secured to the vertebral bodies with fixation screws. The implantable interbody device 200 shown in FIGS. 4 and 5A-5I may be employed in the lumbar or thoracic regions by a midline surgical approach.

Figure 5A:
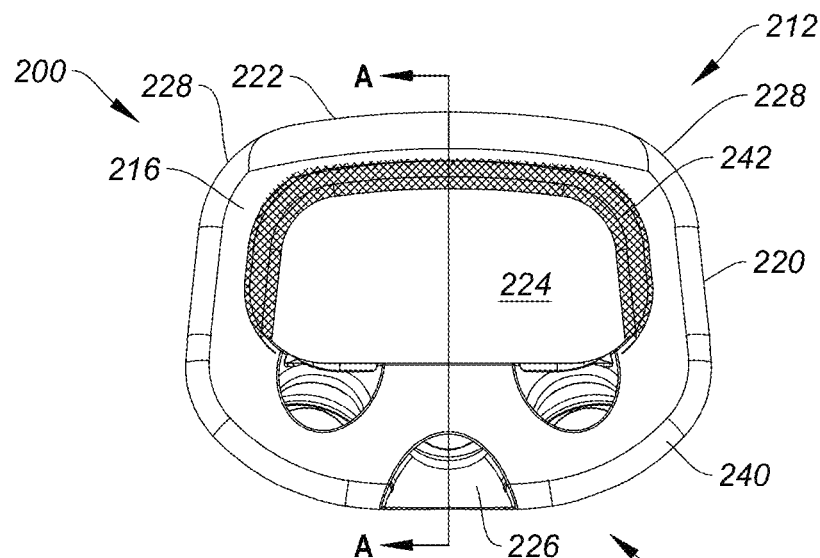
Figure 5B:
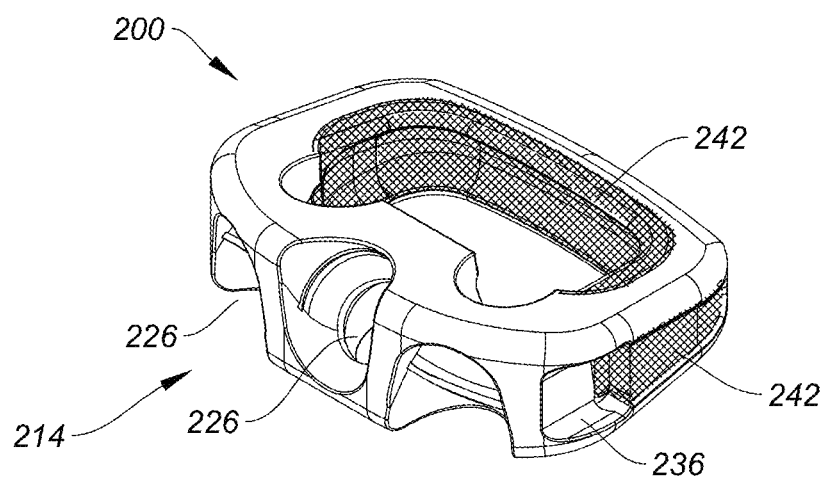
Figure 5C:
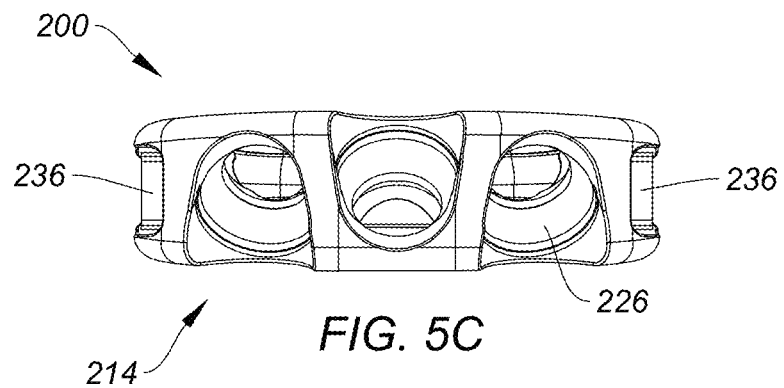
Figure 5D:
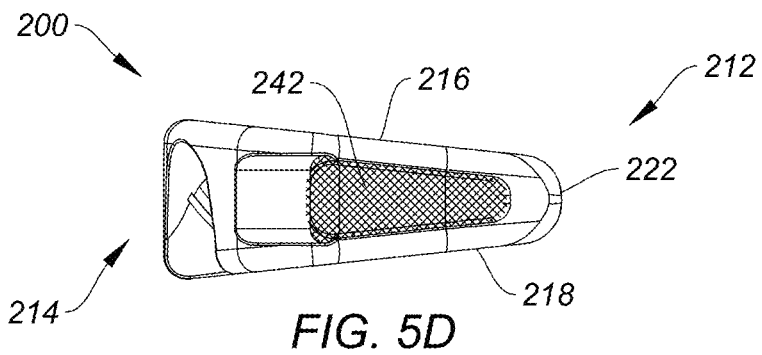
Figure 5E:
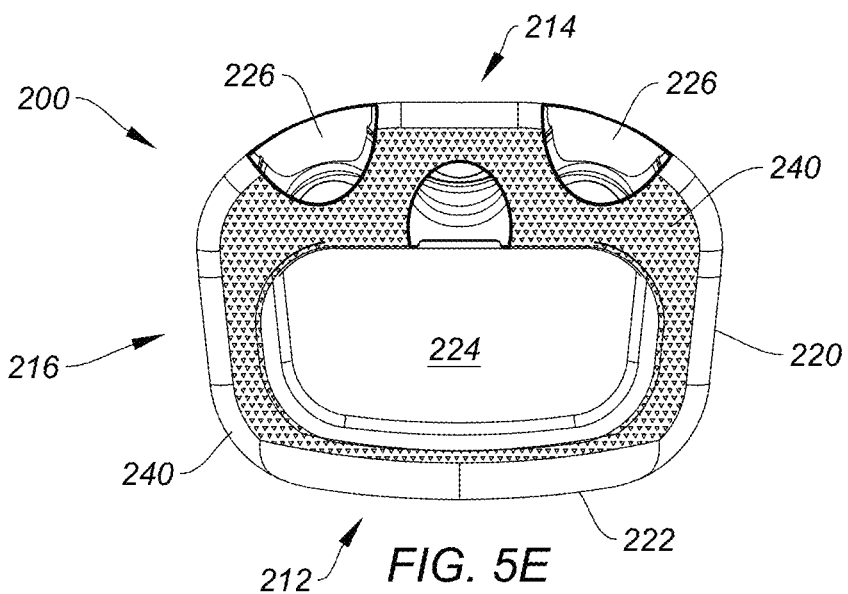
Figure 5F:
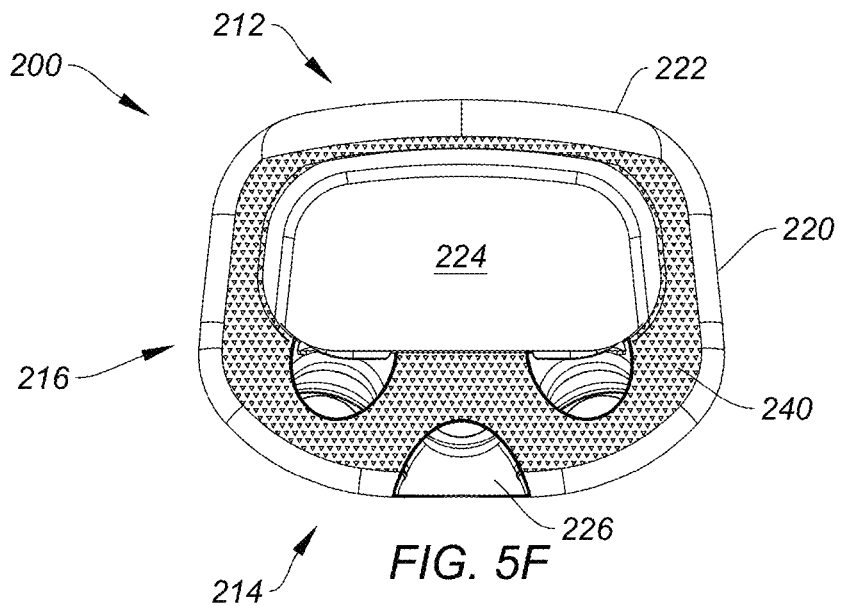

The implantable interbody device 200 may include posterior and anterior portions 212, 214 and upper and lower surfaces 216, 218 profiled to correspond with the profile of any bone material to which they are to be secured. Upper and lower surfaces 216, 218 may be flat or planar, or may be domed or convexly curved. In one embodiment, the implantable device 200 defines a generally wedge shaped structure suitable for a posterior midline insertion approach. As can be seen in FIGS. 5A, 5E and 5F, the device 200 may have an overall trapezoidal shape. Curved sidewalls 220 that extend from the anterior portion 214 intersect with posterior portion 212 at posterolateral corners 228. The corners of the device, including the posterolateral corners 228, may be rounded, smooth or curved, as shown, to avoid marked edges and to provide overall smoothness to the implant profile and prevent undesirable damage to surrounding tissue. The device 200, however, may have other shapes depending on the desired implantation site.

Furthermore, edges of the device 200 may be shaped so as to cooperate with insertion tools to minimize unintended distraction of the vertebral bodies between which the device 200 is being positioned during implantation. For example, as shown in FIGS. 5B and 5C, the implantable device 200 may include grooves or side cutouts 236 to allow a surface for receiving an insertion tool. To facilitate ease of insertion, the posterior portion, or leading end 212 may have a smooth, tapered or angled edge 222 or otherwise shaped edge for concomitant distraction of soft tissue during insertion.

The implantable interbody device 200 may include a central opening or lumen 224 extending between the upper and lower surfaces 216, 218 to facilitate bony ongrowth and bony ingrowth or fusion between adjacent bone segments, such as vertebral bodies. If so desired, the opening 224 may be used to receive and hold bone graft material to further enhance the bone fusion process.

Figure 5G:
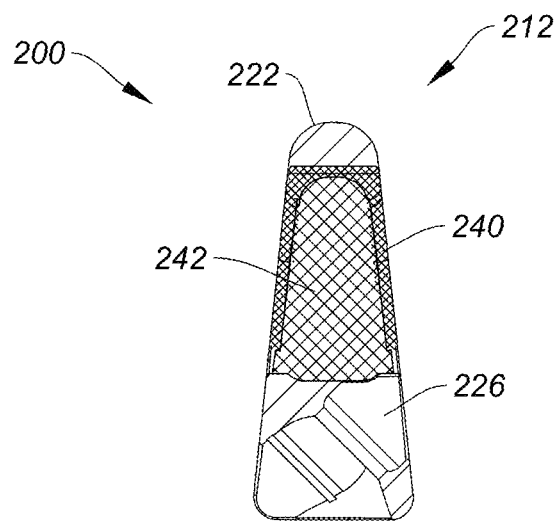
Figure 5H:
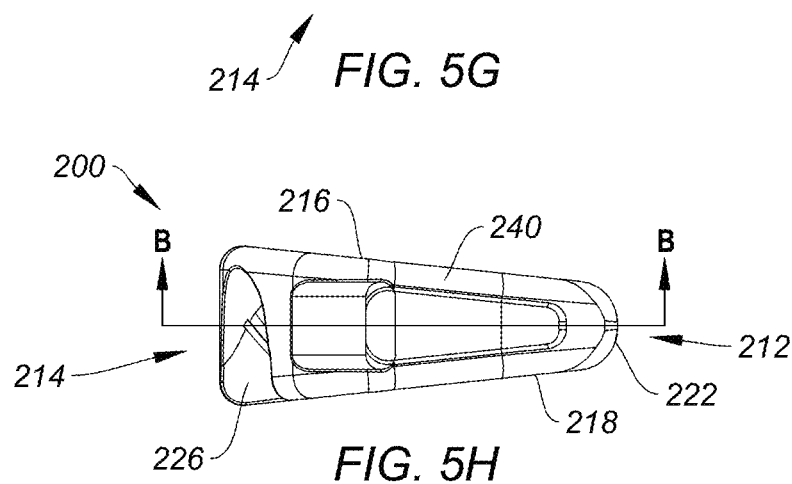
Figure 5I:
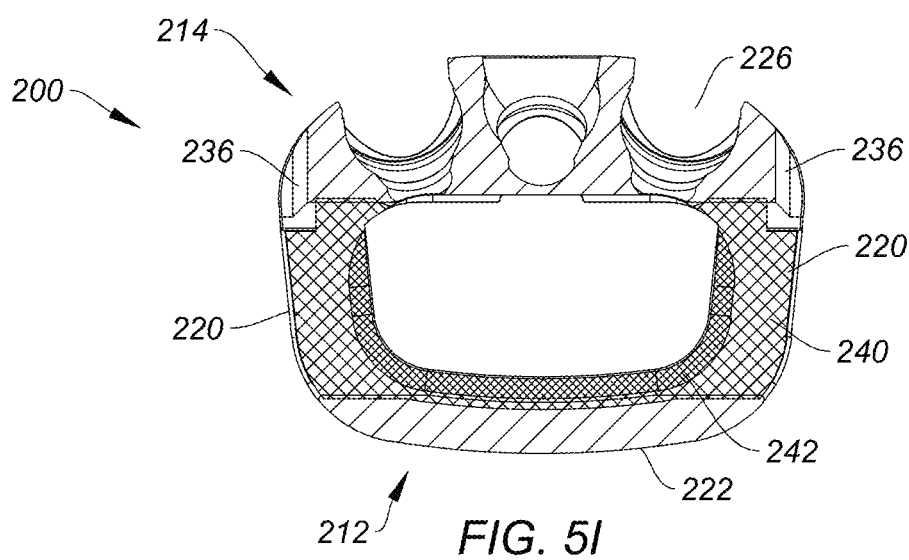

Like device 100, the implantable interbody device 200 may include a porous lattice or mesh component 242 that can be incorporated within the solid scaffold structure 240 of the device 200. For instance, as shown in FIGS. 5E and 5F, the implantable device 200 may have a solid structural component 240 within and on which a porous component 242 may be incorporated, as seen in FIGS. 5A and 5B, to form a combination and resultant device 200 which provides a porous component 242 within a solid structural component 240, as shown in FIGS. 5G and 5I. Accordingly, the implantable interbody device 200 of FIGS. 5A-5I incorporate the same principles of a network of pores and solid surfaces as the device 100 above, to create an improved fusion facilitating device 200 not heretofore seen.

Since the porous component is interconnected to the solid component, greater integration is achieved than with conventional textured coatings, titanium spray coatings, or surface roughenings. These additional surface enhancements are considered optional. For instance, the solid surfaces of the device 200 may be further coated or provided with surface features like roughenings or textures. As shown in FIGS. 5E and 5F, the solid scaffold structure 240 may be formed with a surface texture, and may therefore provide an outer surface that is textured, such as a roughened texture or one with discrete geometric protrusions, to enhance surface attachment.

Figure 4:
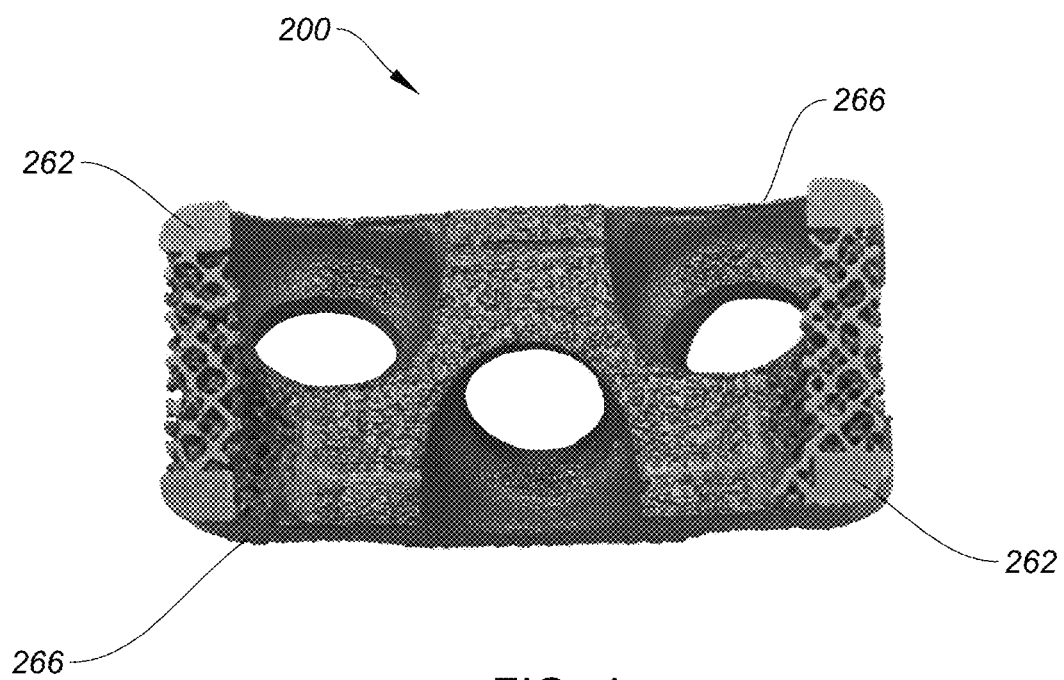

As with device 100, the extensive porous lattice areas 242 that are engineered to extend all the way around the device 200 allow for more interaction with bone than with convention enhancement methods. Such features are possible for metallic, metallic alloy or polymeric devices based on layer-by-layer deposition manufacturing techniques like 3D printing or selective layer melting (SLM) of metal, metal alloy or polymer. And since the entire device 200 may be formed of metal, metal alloy or polymer, no additional visualization markers are necessary for visualization. Because the devices 200 are created in a single process without the need for connecting subcomponents together, one of the key benefits of the devices is that the interface between the porous lattice areas 242 and the upper surface 216, lower surface 218 or sidewalls 220 is seamless and void of mechanical or chemical bonding, adding to the overall strength of the devices 200. As shown in FIG. 4, the body of device 200 incorporates the porous lattice or mesh structures 242 into itself. The porous lattice structure 242 is not a separate panel that is added onto the body, but is integrated into the body of the device 200.

In some embodiments, the sidewalls 220 may be concave to create a unique C- or I-beam shape 262 when viewed in cross-section, which serves to enhance support of the endplates and reduce risk of subsidence, while also being able to promote a lightweight, lower stiffness structure. This unique C- or I-beam cross-sectional shape of the sidewalls 220 also helps to enhance support of any graft material contained within the central opening 224 or of biologics formed to nest within this donut shaped lumen 266. The sidewalls 220 and lumens 266 together may be radiused as shown in FIG. 4 in such a way to create a self-supporting arch and other geometries to reduce the need for additional supports during the manufacturing process, such as when 3D printing.

In some embodiments, the implantable interbody device 200 may have non-parallel upper and lower surfaces 216, 218 to form a wedge-shaped body, if so desired. However, one skilled in the art will appreciate that the implantable interbody device 200 may also be provided with parallel upper and lower surfaces 216, 218. The implantable interbody device 200 may have any suitable shape or size to allow it to be used under lordotic or kyphotic conditions, similar to device 100 above.

Similar to device 100, the anterior portion, or trailing end 214 of the implantable interbody device 200 can include holes 226 for receiving fixation elements, such as for example, bone screws to secure the device 200 to adjacent bone tissue. In the embodiment shown, the device 200 can include three holes 226, such as one hole being centrally located (i.e., along the center line), and two laterally located (i.e., beside the center line.) Without compromising stability, the lateral holes 226 should be located in a manner that avoids the need to retract vessels during surgery. It has been postulated that extended retraction of vessels during surgery may lead to greater chances for complications to the patient. The lateral holes 226 should also be positioned so as to provide easier visibility of the surrounding implantation site for the surgeon. One skilled in the art will appreciate that the device 200 may comprise any number of holes at any location on the device 200, or may have no screw holes at all, as shown in the embodiments of FIGS. 6A-6I.

The holes 226 of device 200 are similar to those holes 126 of device 100 and share the same features described above. Accordingly, holes 226 also provide a path through which securing means (e.g., fixation elements such as bone screws) may be inserted so as to secure the device 200 to respective superior and inferior vertebral bodies. The holes 226 may be configured to accommodate a variety of securing means, such as screws, pins, staples, or any other suitable fastening device. In one embodiment, the fixation screws may be self-tapping and/or self-drilling and may be of a bone-screw-type, such as those well known to skilled artisans. The screws can be sized and shaped for unicortical or bicortical bone fixation. In addition, in some embodiments, the screw holes 226 may be hourglass shaped. Furthermore, the screw holes 226 may include a screw hole indicator groove, screw hole direction indicator arrow, a reverse chamfer or overhang feature, countersink, visual response feedback feature, and/or tactile response feedback feature, similar to the screw holes described in U.S. patent application Ser. No. 15/428, 601, now U.S. Patent Application Publication No. US2017/0239061 A1, the contents of which are hereby incorporated by reference.

FIGS. 6A to 6I illustrate another exemplary embodiment of an implantable interbody device 200' that may be implanted in the intervertebral space between vertebral bodies by a midline approach, without the need for additional screw fixation. The implantable interbody device 200' shares similar features to the implantable interbody device 200 of FIGS. 4 and 5A-5I, with like features having the same reference number followed by the symbol "'" for convenient reference. Like the implantable interbody device 200 previously described, device 200' may also be employed in the lumbar or thoracic regions.

Figure 6A:
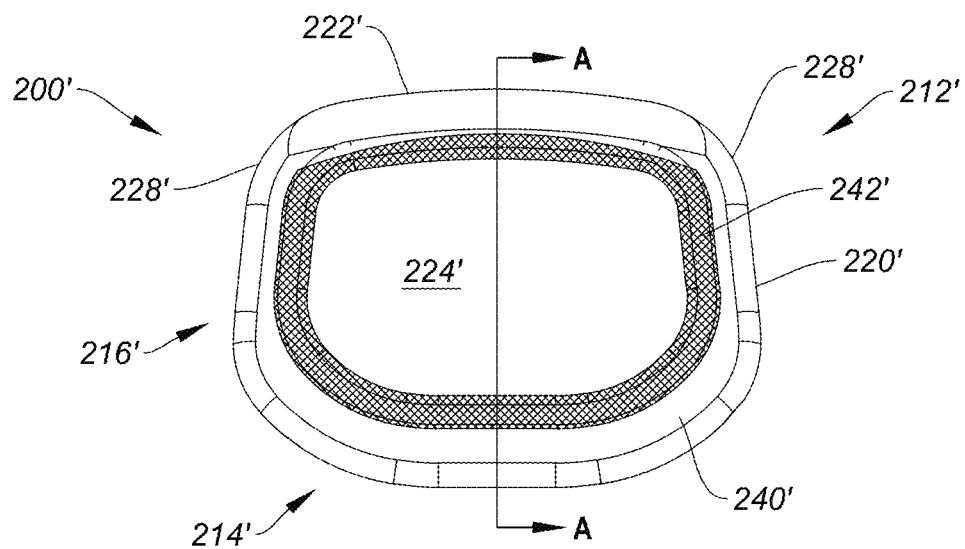
Figure 6B:
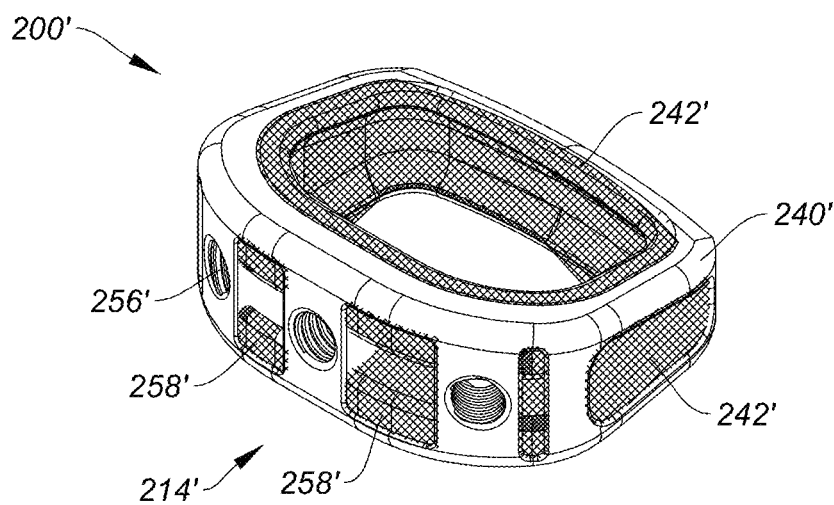
Figure 6C:
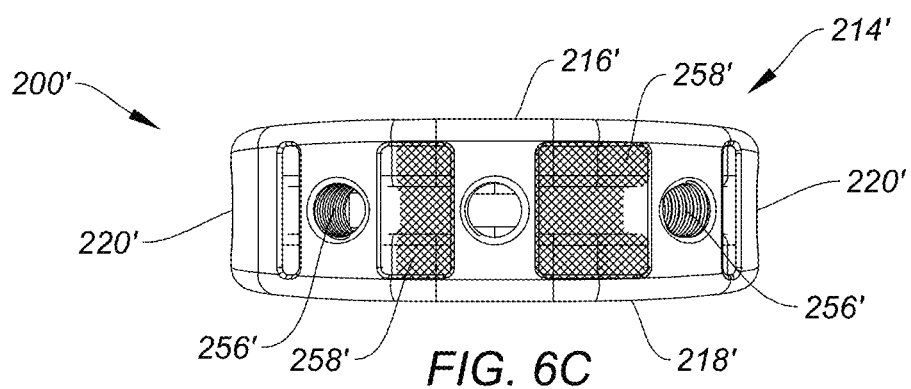
Figure 6D:
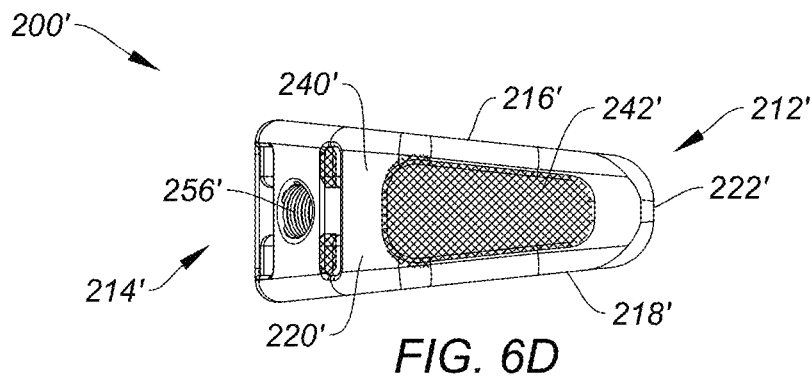
Figure 6E:
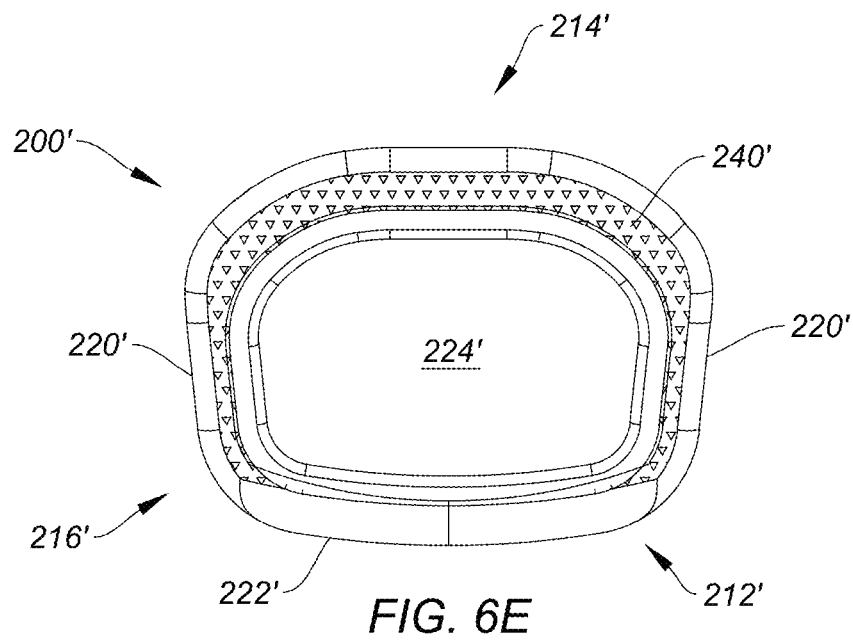
Figure 6F:
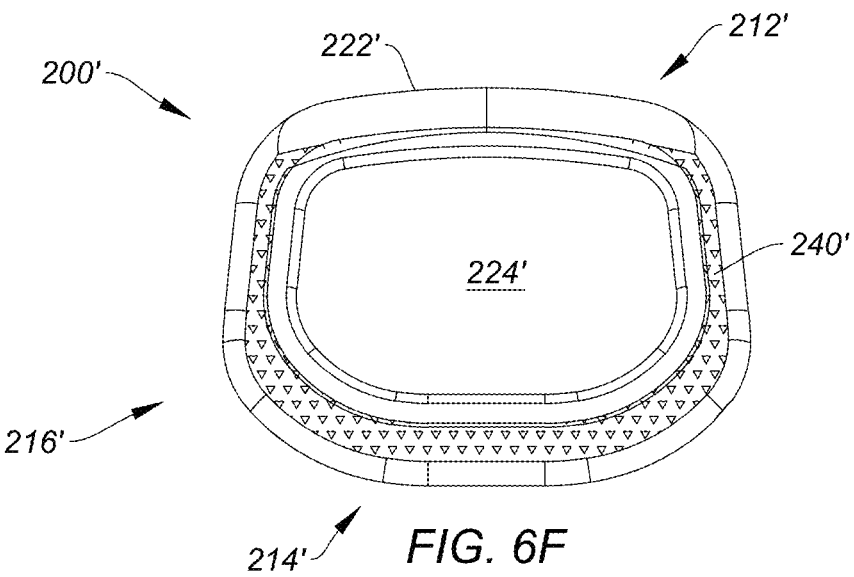

The implantable interbody device 200' may include posterior and anterior portions 212', 214' and upper and lower surfaces 216', 218' profiled to correspond with the profile of any bone material to which they are to be secured. Upper and lower surfaces 216', 218' may be flat or planar, or may be domed or convexly curved. In one embodiment, the implantable device 200' defines a generally wedge shaped structure suitable for a posterior midline insertion approach. As can be seen in FIGS. 6A, 6E and 6F, the device 200' may have an overall trapezoidal shape. Curved sidewalls 220' that extend from the anterior portion 214' intersect with posterior portion 212' at posterolateral corners 228'. The corners of the device 200', including the posterolateral corners 228', may be rounded, smooth or curved, as shown, to avoid marked edges and to provide overall smoothness to the implant profile and prevent undesirable damage to surrounding tissue. The device 200', however, may have other shapes depending on the desired implantation site.

Furthermore, edges of the device 200' may be shaped so as to cooperate with insertion tools to minimize unintended distraction of the vertebral bodies between which the device 200' is being positioned during implantation. For example, as shown in FIGS. 6B and 6C, the implantable device 200' may include grooves or side cutouts 236' to allow a surface for receiving an insertion tool. To facilitate ease of insertion, the posterior portion, or leading end 212' may have a smooth, tapered or angled edge 222' or otherwise shaped edge for concomitant distraction of soft tissue during insertion.

The implantable interbody device 200' may include a central opening or lumen 224' extending between the upper and lower surfaces 216', 218' to facilitate bony ongrowth and bony ingrowth or fusion between adjacent bone segments, such as vertebral bodies. If so desired, the opening 224' may be used to receive and hold bone graft material to further enhance the bone fusion process.

Figure 6G:
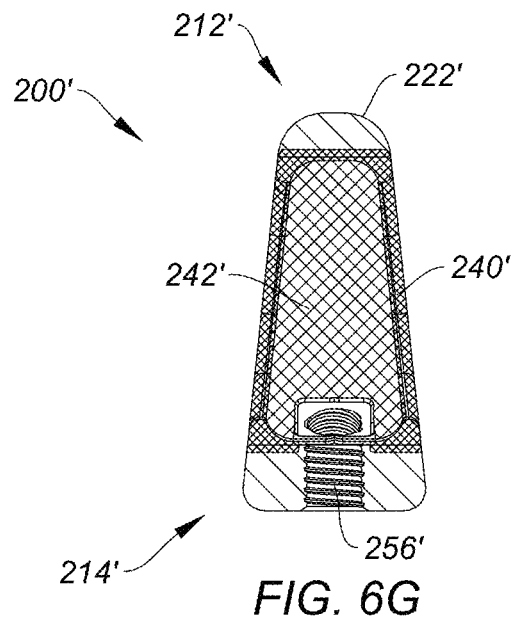
Figure 6H:
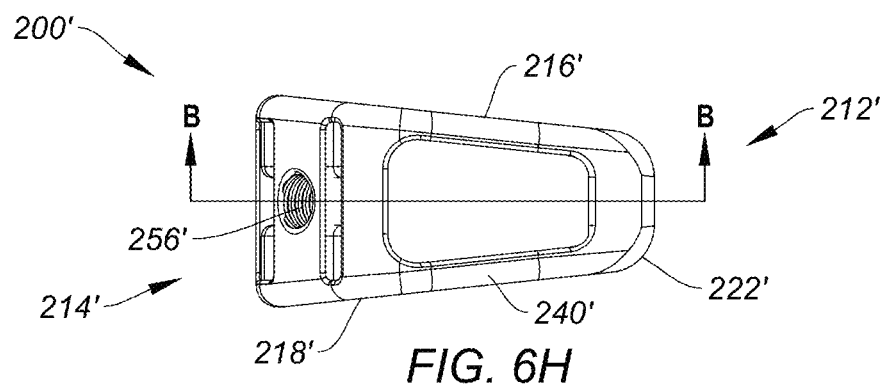
Figure 6I:
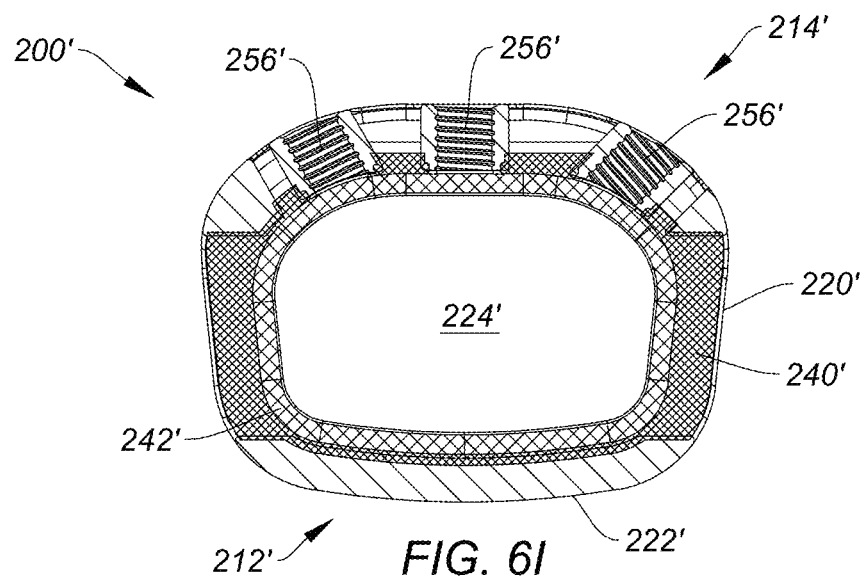

Like device 200, the implantable interbody device 200' may include a porous lattice or mesh component 242' that can be incorporated within the solid scaffold structure 240' of the device 200'. For instance, as shown in FIGS. 6E and 6F, the implantable device 200' may have a solid structural component 240' within and on which a porous component 242' may be incorporated, as seen in FIGS. 6A and 6B, to form a combination and resultant device 200' which provides a porous component 242' within a solid structural component 240', as shown in FIGS. 6G and 6I. Accordingly, the implantable interbody device 200' of FIGS. 6A-6I incorporate the same principles of a network of pores and solid surfaces as the device 100 above, to create an improved fusion facilitating device 200' not heretofore seen. Since the porous component is interconnected to the solid component, greater integration is achieved than with conventional textured coatings, titanium spray coatings, or surface roughenings. These additional surface enhancements are considered optional. For instance, the solid surfaces of the device 200' may be further coated or provided with surface features like roughenings or textures. As shown in FIGS. 6E and 6F, the solid scaffold structure 240' may be formed with a surface texture, and may therefore provide an outer surface that is textured, such as a roughened texture or one with discrete geometric protrusions, to enhance surface attachment.

In some embodiments, the sidewalls 220' may be concave to create a unique C- or I-beam shape when viewed in cross-section, which serves to enhance support of the endplates and reduce risk of subsidence, while also being able to promote a lightweight, lower stiffness structure. This unique C- or I-beam cross-sectional shape of the sidewalls 220' also helps to enhance support of any graft material contained within the central opening 224' or of biologics formed to nest within this donut shaped lumen. The sidewalls and lumens together may be radiused in such a way to create a self-supporting arch and other geometries to reduce the need for additional supports during the manufacturing process, such as when 3D printing.

In some embodiments, the implantable interbody device 200' may have non-parallel upper and lower surfaces 216', 218' to form a wedge-shaped body, if so desired. However, one skilled in the art will appreciate that the implantable interbody device 200' may also be provided with parallel upper and lower surfaces 216', 218'. The implantable interbody device 200' may have any suitable shape or size to allow it to be used under lordotic or kyphotic conditions, similar to device 100 above.

Unlike implantable device 200, the implantable device 200' of the present embodiment does not include any angular screw holes at its anterior portion, or trailing end 214'. Instead, the implantable device 200' of the present embodiment may include holes 256' as shown in FIGS. 6B, 6C, 6D, and 6G-6I. The hole 256' may be threaded, as shown. These threaded holes 256' may be used for attachment of an inserter tool, or a threaded nut or screw to secure a graft component. The additional thread form enables easy oblique insertion during surgery. In addition, the threaded screw holes 256' allow for a larger graft area in the central opening 224'. Additionally, the anterior portion 214' may include regions 258' where the porous component 242' may be provided, as shown in FIGS. 6B and 6C.

Implantable Interbody Devices for the Cervical Spine

As shown in FIGS. 7A-7H and 8A-8H, exemplary embodiments of an implantable spinal fusion or interbody device 300, 300' configured for the cervical spine can be provided in accordance with the principles of the present disclosure.

FIGS. 7A to 7H illustrate an exemplary embodiment of an implantable interbody device 300 that may be implanted in the intervertebral space between vertebral bodies of the cervical spine and secured to the vertebral bodies with fixation screws. The device 300 may be sized and shaped to allow stacking at different spinal levels.

Figure 7A:
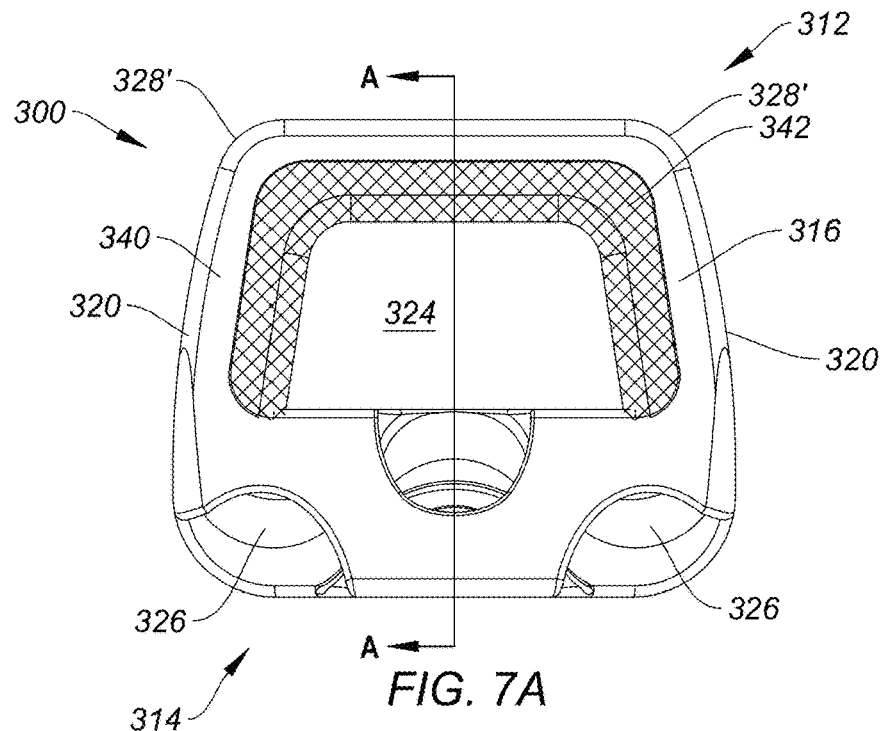
Figure 7B:
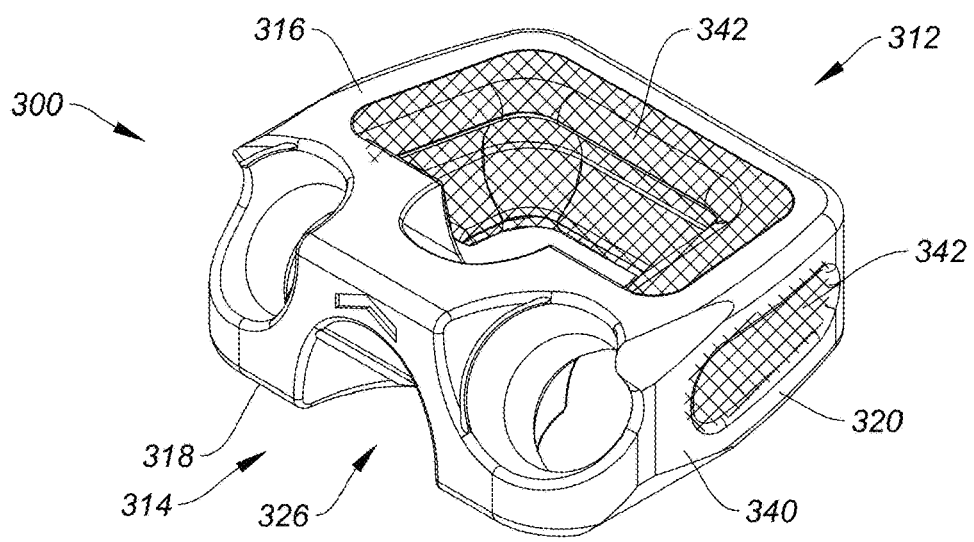
Figure 7C:
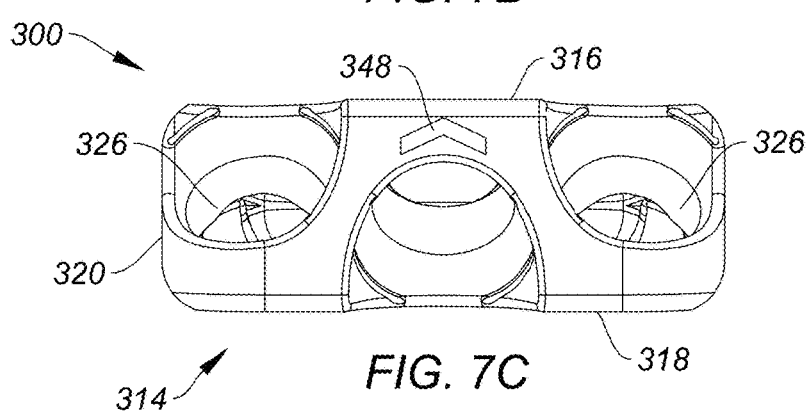
Figure 7D:
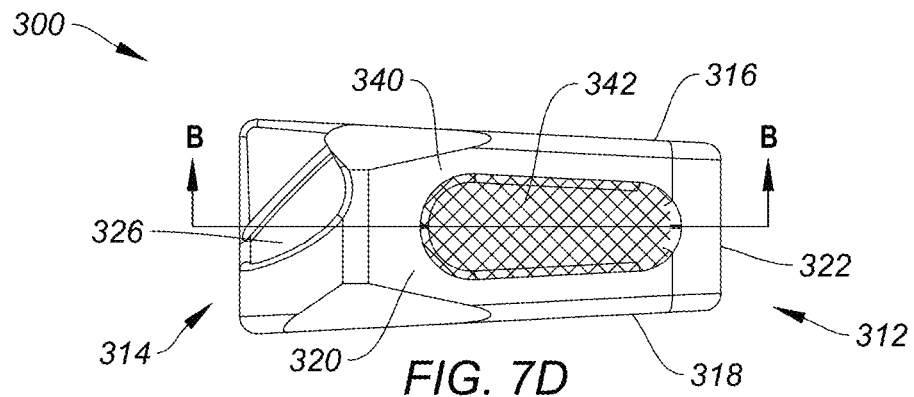
Figure 7E:
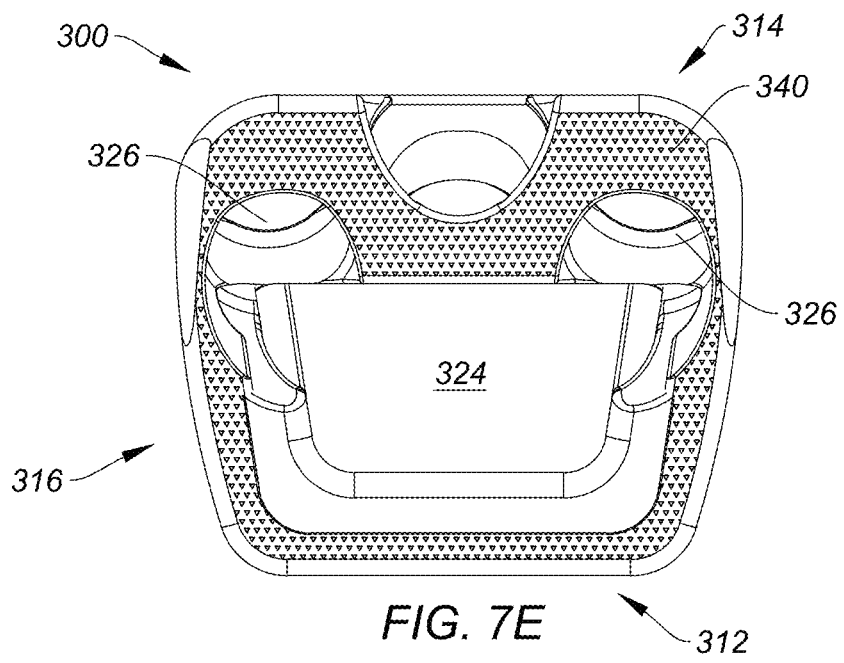
Figure 7F:
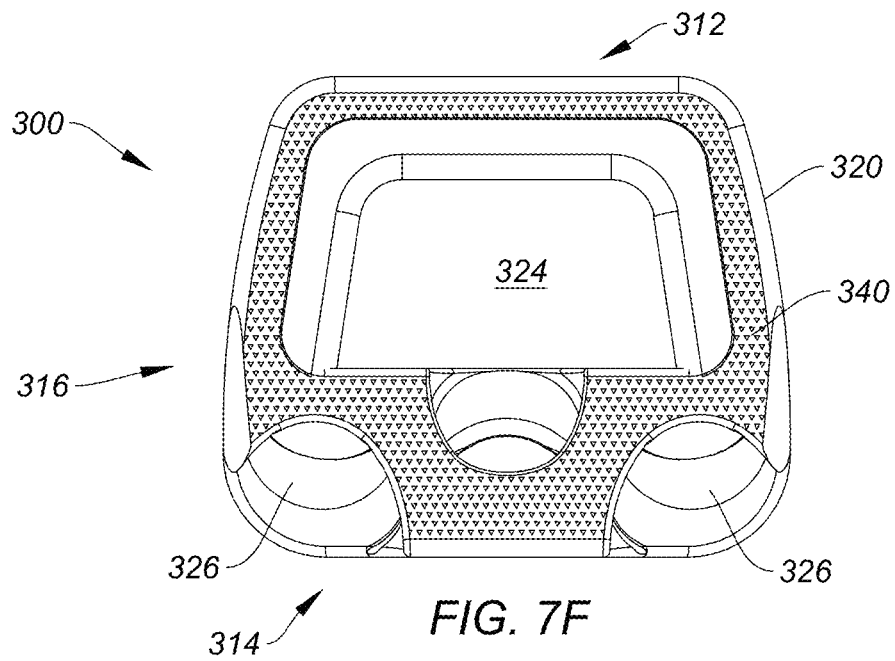

The implantable interbody device 300 adopts similar features from the implantable interbody device 200 described above. Accordingly the device 300 may include posterior and anterior portions 312, 314 and upper and lower surfaces 316, 318 profiled to correspond with the profile of any bone material to which they are to be secured. Upper and lower surfaces 316, 318 may be flat or planar, or may be domed or convexly curved. In one embodiment, the implantable device 300 defines a generally wedge shaped structure suitable for a posterior midline insertion approach. As can be seen in FIGS. 7A, 7E and 7F, the device 300 may have an overall trapezoidal shape. Curved sidewalls 320 that extend from the anterior portion 314 intersect with posterior portion 312 at posterolateral corners 328 similar to device 200. The corners of the device 300, including the posterolateral corners 328, may be rounded, smooth or curved, as shown, to avoid marked edges and to provide overall smoothness to the implant profile and prevent undesirable damage to surrounding tissue. The device 300, however, may have other shapes depending on the desired implantation site.

Furthermore, edges of the device 300 may be shaped so as to cooperate with insertion tools to minimize unintended distraction of the vertebral bodies between which the device 300 is being positioned during implantation. To facilitate ease of insertion, the posterior portion, or leading end 312 may have a smooth, tapered or angled edge 322 or otherwise shaped edge for concomitant distraction of soft tissue during insertion.

The implantable interbody device 300 may include a central opening or lumen 324 extending between the upper and lower surfaces 316, 318 to facilitate bony ongrowth and/or bony ingrowth or fusion between adjacent bone segments, such as vertebral bodies. If so desired, the opening 324 may be used to receive and hold bone graft material to further enhance the bone fusion process.

Figure 7G:
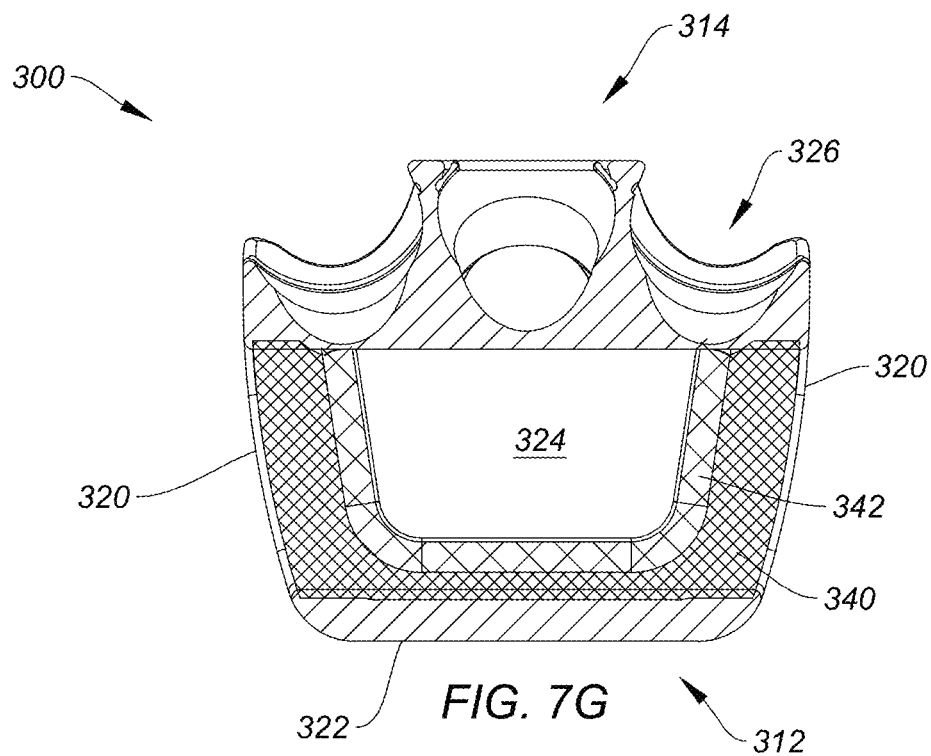
Figure 7H:
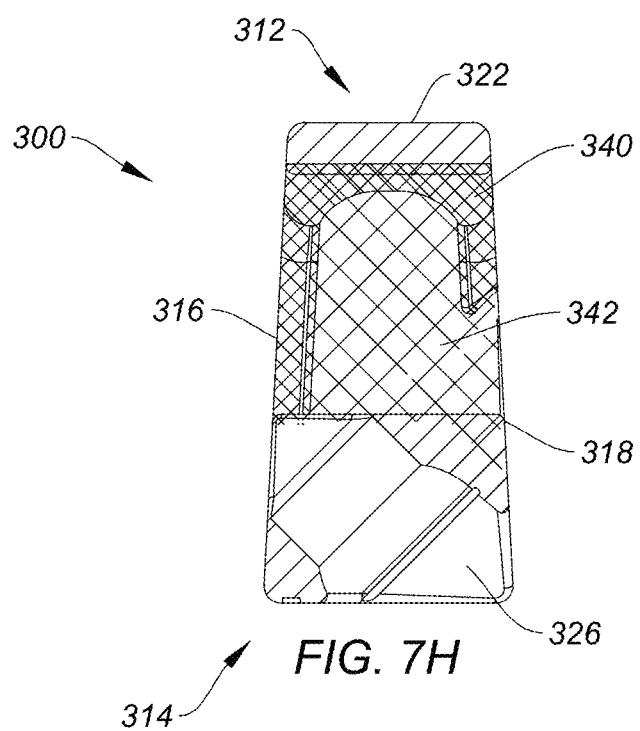

The implantable interbody device 300 may include a porous lattice or mesh component 342 that can be incorporated within the solid scaffold structure 340 of the device 300. For instance, as shown in FIGS. 7E and 7F, the implantable device 300 may have a solid structural component 340 within and on which a porous component 342 may be incorporated, as seen in FIGS. 7A and 7B, to form a combination and resultant device 300 which provides a porous component 342 within a solid structural component 340, as shown in FIGS. 7G and 7H. Accordingly, the implantable interbody device 300 of FIGS. 7A-7H incorporate the same principles of a network of pores and solid surfaces as the devices 100, 200 above, to create an improved fusion facilitating device 300 for the cervical spine not heretofore seen.

Since the porous component is interconnected to the solid component, greater integration is achieved than with conventional textured coatings, titanium spray coatings, or surface roughenings. These additional surface enhancements are considered optional. For instance, the solid surfaces of the device 300 may be further coated or provided with surface features like roughenings or textures. As shown in FIGS. 7E and 7F, the solid scaffold structure 340 may be formed with a surface texture, and may therefore provide an outer surface that is textured, such as a roughened texture or one with discrete geometric protrusions, to enhance surface attachment.

Like devices 100, 200, the extensive porous lattice areas 342 that are engineered to extend all the way around the device 300 allow for more interaction with bone than with convention enhancement methods. Such features are possible for metallic, metallic alloy or polymeric devices based on layer-by-layer deposition manufacturing techniques like 3D printing or selective layer melting (SLM) of metal, metal alloy or polymer. And since the entire device 300 may be formed of metal, metal alloy or polymer, no additional visualization markers are necessary for visualization. Because the devices 300 are created in a single process without the need for connecting subcomponents together, one of the key benefits of the devices is that the interface between the porous lattice areas 342 and the upper surface 316, lower surface 318 or sidewalls 320 is seamless and void of mechanical or chemical bonding, adding to the overall strength of the devices 300. As shown, the body of device 300 incorporates the porous lattice or mesh structures 342 into itself. The porous lattice structure 342 is not a separate panel that is added onto the body, but is integrated into the body of the device 300.

In some embodiments, the sidewalls 320 may be concave to create a unique C- or I-beam shape when viewed in cross-section, which serves to enhance support of the endplates and reduce risk of subsidence, while also being able to promote a lightweight, lower stiffness structure. This unique C- or I-beam cross-sectional shape of the sidewalls also helps to enhance support of any graft material contained within the central opening 324 or of biologics formed to nest within this donut shaped lumen. The sidewalls 320 and lumens together may be radiused in such a way to create a self-supporting arch and other geometries to reduce the need for additional supports during the manufacturing process, such as when 3D printing.

In some embodiments, the implantable interbody device 300 may have non-parallel upper and lower surfaces 316, 318 to form a wedge-shaped body. However, one skilled in the art will appreciate that the implantable interbody device 300 may also be provided with parallel upper and lower surfaces 316, 318. The implantable interbody device 300 may have any suitable shape or size to allow it to be used under lordotic or kyphotic conditions, similar to devices 100, 200 above.

Also like devices 100, 200, the anterior portion, or trailing end 314 of the implantable interbody device 300 can include holes 326 for receiving fixation elements, such as for example, bone screws to secure the device 300 to adjacent bone tissue. In the embodiment shown, the device 300 may include three holes 326, such as one hole being centrally located (i.e., along the center line), and two laterally located (i.e., beside the center line.) Without compromising stability, the lateral holes 326 should be located in a manner that avoids the need to retract vessels during surgery. It has been postulated that extended retraction of vessels during surgery may lead to greater chances for complications to the patient. The lateral holes 326 should also be positioned so as to provide easier visibility of the surrounding implantation site for the surgeon. One skilled in the art will appreciate that the device 300 may comprise any number of holes at any location on the device 300, or may have no screw holes at all, as shown in the embodiments of FIGS. 8A-8H.

The holes 326 of device 300 are similar to those holes 126, 226 of devices 100, 200 and share the same features described above. Accordingly, holes 326 also provide a path through which securing means (e.g., fixation elements such as bone screws) may be inserted so as to secure the device 300 to respective superior and inferior vertebral bodies. The holes 326 may be configured to accommodate a variety of securing means, such as screws, pins, staples, or any other suitable fastening device. In one embodiment, the fixation screws may be self-tapping and/or self-drilling and may be of a bone-screw-type, such as those well known to skilled artisans. The screws can be sized and shaped for unicortical or bicortical bone fixation. In addition, in some embodiments, the screw holes 326 may be hourglass shaped. Furthermore, the screw holes 326 may include a screw hole indicator groove, screw hole direction indicator arrow, a reverse chamfer or overhang feature, countersink, visual response feedback feature, and/or tactile response feedback feature, similar to the screw holes described in U.S. patent application Ser. No. 15/428,601, now U.S. Patent Application Publication No. US2017/0239061 A1, the contents of which are hereby incorporated by reference.

According to other aspects of the disclosure, the device 300 may include visual cues 348 like arrows to indicate screw trajectory. The unique hybrid scaffold structure of the device 300 enables better graft retention with its concavity. Furthermore, as shown, the textured exterior surface enhances bone attachment and bone fusion. As with devices 100, 200, the device may further include additional surface enhancements such as coatings, surface textures or surface roughenings.

FIGS. 8A to 8H illustrate another exemplary embodiment of an implantable interbody device 300' that may be implanted in the intervertebral space between vertebral bodies of the cervical spine, without the need for additional screw fixation. The implantable interbody device 300' shares similar features to the implantable interbody device 300 of FIGS. 7A-7H, with like features having the same reference number followed by the symbol "'" for convenient reference.

Figure 8A:
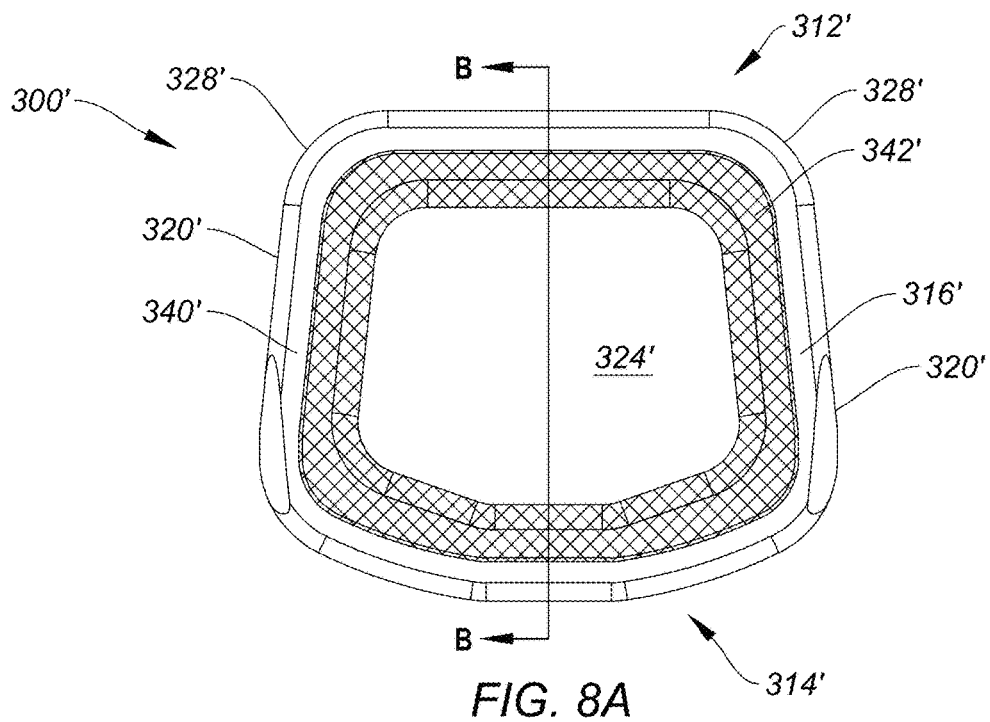
Figure 8B:
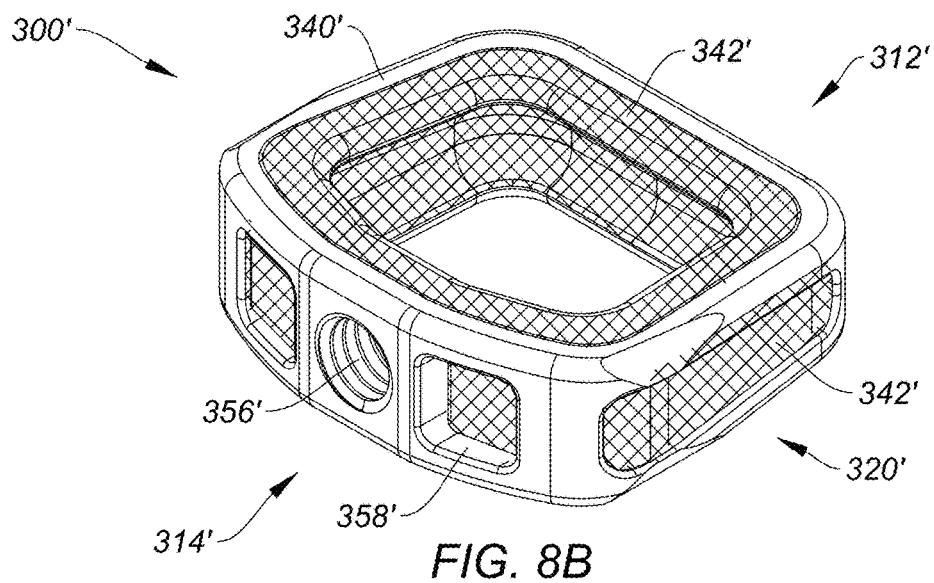
Figure 8C:
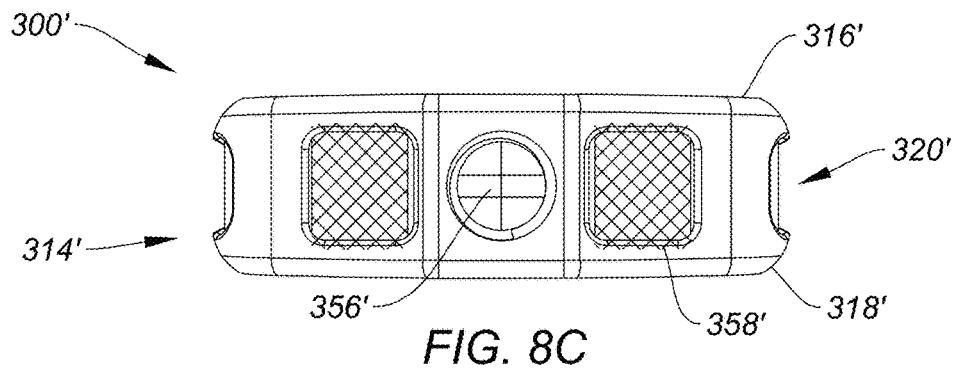
Figure 8D:
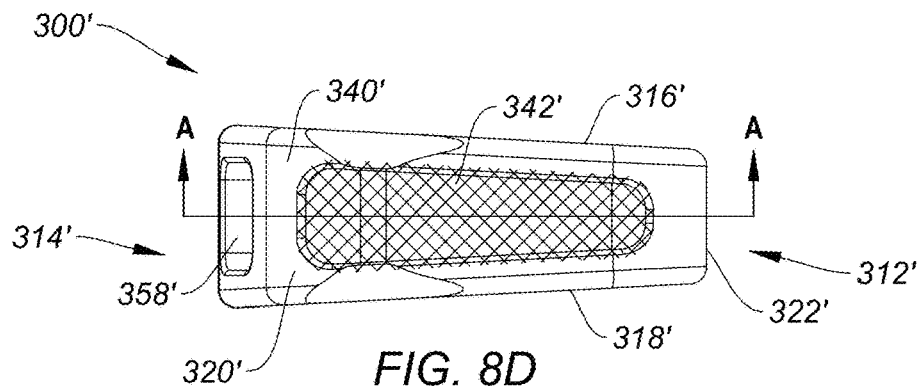
Figure 8E:
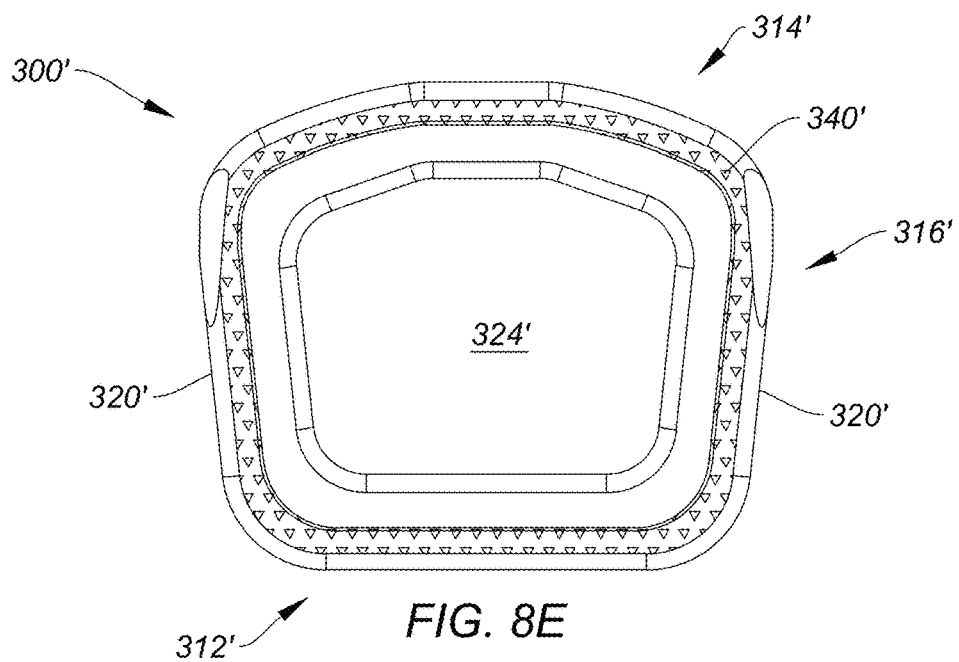
Figure 8F:
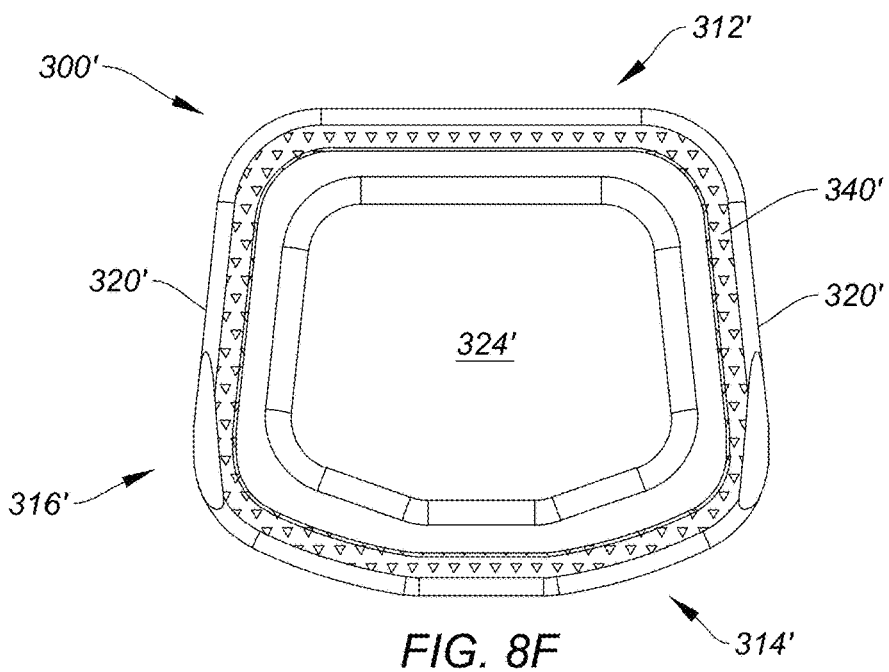

Similar to implantable interbody device 300, the implantable interbody device 300' may include posterior and anterior portions 312', 314' and upper and lower surfaces 316', 318' profiled to correspond with the profile of any bone material to which they are to be secured. Upper and lower surfaces 316', 318' may be flat or planar, or may be domed or convexly curved. In one embodiment, the implantable device 300' defines a generally wedge shaped structure suitable for a posterior midline insertion approach. As can be seen in FIGS. 8A, 8E and 8F, the device 300' may have an overall trapezoidal shape. Curved sidewalls 320' that extend from the anterior portion 314' intersect with posterior portion 312' at posterolateral corners 328'. The corners of the device 300', including the posterolateral corners 328', may be rounded, smooth or curved, as shown, to avoid marked edges and to provide overall smoothness to the implant profile and prevent undesirable damage to surrounding tissue. The device 300', however, may have other shapes depending on the desired implantation site. The device 300', however, may have other shapes depending on the desired implantation site.

Furthermore, edges of the device 300' may be shaped so as to cooperate with insertion tools to minimize unintended distraction of the vertebral bodies between which the device 300' is being positioned during implantation. To facilitate ease of insertion, the posterior portion, or leading end 312' may have a smooth, tapered or angled edge 322' or otherwise shaped edge for concomitant distraction of soft tissue during insertion.

The implantable interbody device 300' may include a central opening or lumen 324' extending between the upper and lower surfaces 316', 318' to facilitate bony ongrowth and/or bony ingrowth or fusion between adjacent bone segments, such as vertebral bodies. If so desired, the opening 324' may be used to receive and hold bone graft material to further enhance the bone fusion process.

Figure 8G:
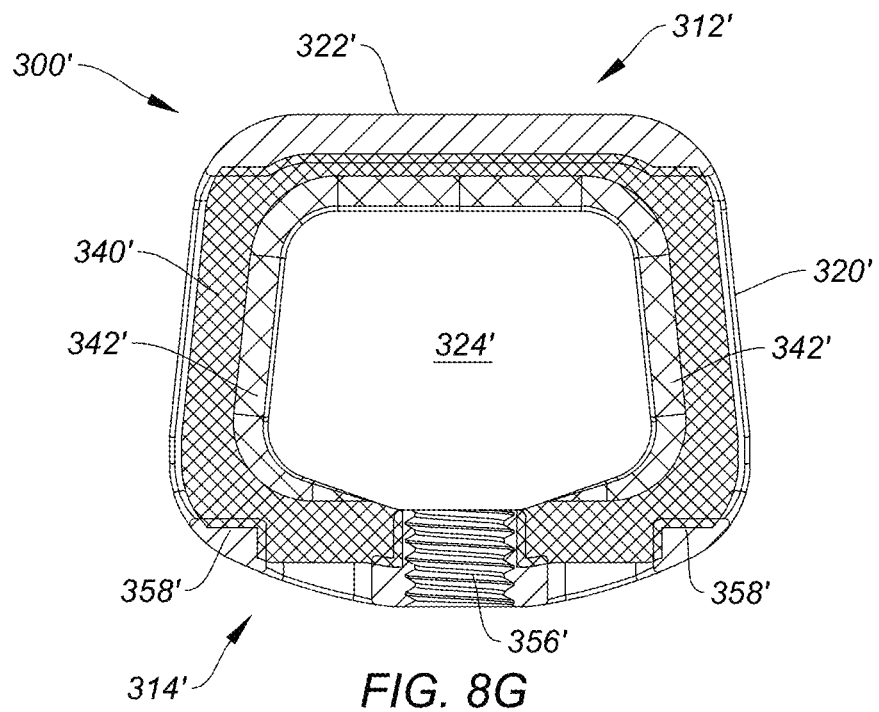
Figure 8H:
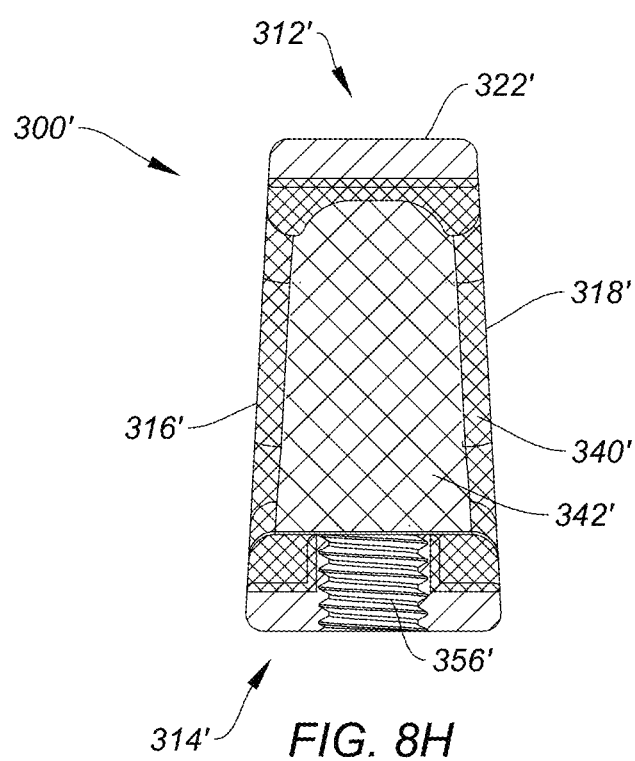

The implantable interbody device 300' may include a porous lattice or mesh component 342' that can be incorporated within the solid scaffold structure 340' of the device 300'. For instance, as shown in FIGS. 8E and 8F, the implantable device 300' may have a solid structural component 340' within and on which a porous component 342' may be incorporated, as seen in FIGS. 8A and 8B, to form a combination and resultant device 300' which provides a porous component 342' within a solid structural component 340', as shown in FIGS. 8G and 8H. Accordingly, the implantable interbody device 300' of FIGS. 8A-8H incorporate the same principles of a network of pores and solid surfaces as the devices 100, 200 above, to create an improved fusion facilitating device 300' for the cervical spine not heretofore seen.

Since the porous component is interconnected to the solid component, greater integration is achieved than with conventional textured coatings, titanium spray coatings, or surface roughenings. These additional surface enhancements are considered optional. For instance, the solid surfaces of the device 300' may be further coated or provided with surface features like roughenings or textures. As shown in FIGS. 8E and 8F, the solid scaffold structure 340' may be formed with a surface texture, and may therefore provide an outer surface that is textured, such as a roughened texture or one with discrete geometric protrusions, to enhance surface attachment.

Like devices 100, 200, the extensive porous lattice areas 342' that are engineered to extend all the way around the device 300' allow for more interaction with bone than with convention enhancement methods. Such features are possible for metallic, metallic alloy or polymeric devices based on layer-by-layer deposition manufacturing techniques like 3D printing or selective layer melting (SLM) of metal, metal alloy or polymer. And since the entire device 300' may be formed of metal, metal alloy or polymer, no additional visualization markers are necessary for visualization. Because the devices 300' are created in a single process without the need for connecting subcomponents together, one of the key benefits of the devices is that the interface between the porous lattice areas 342' and the upper surface 316', lower surface 318' or sidewalls 320' is seamless and void of mechanical or chemical bonding, adding to the overall strength of the devices 300'. As shown, the body of device 300' incorporates the porous lattice or mesh structures 342' into itself. The porous lattice structure 342' is not a separate panel that is added onto the body, but is integrated into the body of the device 300'.

In some embodiments, the sidewalls 320' may be concave to create a unique C- or I-beam shape when viewed in cross-section, which serves to enhance support of the endplates and reduce risk of subsidence, while also being able to promote a lightweight, lower stiffness structure. This unique C- or I-beam cross-sectional shape of the sidewalls also helps to enhance support of any graft material contained within the central opening 324' or of biologics formed to nest within this donut shaped lumen. The sidewalls 320' and lumens together may be radiused in such a way to create a self-supporting arch and other geometries to reduce the need for additional supports during the manufacturing process, such as when 3D printing.

In some embodiments, the implantable interbody device 300' may have non-parallel upper and lower surfaces 316', 318' to form a wedge-shaped body. However, one skilled in the art will appreciate that the implantable interbody device 300' may also be provided with parallel upper and lower surfaces 316', 318'. The implantable interbody device 300' may have any suitable shape or size to allow it to be used under lordotic or kyphotic conditions, similar to devices 100, 200 above.

Unlike implantable device 300, the implantable device 300' of the present embodiment does not include any angular screw holes at its anterior portion, or trailing end 314'. Instead, the implantable device 300' of the present embodiment may include a holes 356' as shown in FIGS. 8B, 8C, 8G and 8H. The hole 356' may be threaded, as shown. These threaded holes 356' may be used for attachment of an inserter tool, or a threaded nut or screw to secure a graft component. The additional thread form enables easy oblique insertion during surgery. In addition, the threaded screw holes 356' allow for a larger graft area in the central opening 324'. Additionally, the anterior portion 314' may include regions 358' where the porous component 342' may be provided, as shown in FIGS. 8B and 8C.

Implantable Interbody Devices for Lateral-Oblique Approach

As shown in FIGS. 9A-9E and 10A-10E, exemplary embodiments of implantable spinal fusion or interbody devices 400, 400' configured for lateral-oblique insertion into the contra lateral and posterior space of the spine can be provided in accordance with the principles of the present disclosure. The implantable interbody devices 400, 400' shown in FIGS. 9A-9E and FIGS. 10A-10E may be employed in the lumbar or thoracic regions in a lateral-oblique surgical approach.

FIGS. 9A to 9E illustrate an exemplary embodiment of an implantable interbody device 400 configured for lateral-oblique insertion into the contra lateral and posterior space of the spine. The implantable device 400 may be implanted in the intervertebral space between vertebral bodies and secured to the vertebral bodies with fixation screws. As mentioned, the implantable interbody device 400 may be configured for insertion at an oblique angle into contra lateral and posterior space of the spine. The implantable interbody device 400 may be employed in the lumbar region of the spine. However, it is contemplated that the implantable interbody device 400 may be shaped and sized for use in other areas of the spine as well, such as the thoracic and the cervical region of the spine.

Additionally, while the devices 400 of the present disclosure are described as being inserted using an oblique angle approach, it is understood that the devices 400 may also be properly inserted using other techniques as well, including approaches that are not oblique angle approaches. For example, where the shape and geometry of the implantable interbody device 400 is suited for use in a clinical application but the oblique angle approach is not necessary or desired, then it is understood that the implantable interbody device 400 may be employed, without restriction to the particular surgical technique to insert the implantable interbody device 400. In some instances, different spinal levels may require a different insertion approach but would still be able to utilize the devices 400 of the present disclosure. Therefore, the devices 400 may be used at multiple levels, whereby the implants may be inserted at these levels with different approaches.

Turning now to the drawings, according to one exemplary embodiment, the implantable interbody device 400 may include posterior and anterior portions 412, 414, and upper and lower surfaces 416, 418 connected by two lateral walls or sidewalls 420a, 420b and an intermediate wall segment or sidewall 420c. Upper and lower surfaces 416, 418 may be flat or planar, or may be domed or convexly curved. The two lateral walls or sidewalls 420a, 420b may converge into a nose or tip 422. This nose or tip 422 may be rounded or tapered. Collectively, the three walls 420a, 420b, 420c may together form a generally triangular profile. However, as shown, one lateral wall 420b may be greater in length than the other lateral wall 420a, creating a shark's fin-like shape. Additionally, the walls collectively may also form a rounded or approximately rectangular shape, particularly if one or more of the walls is curved or angled itself.

As shown, the implantable interbody device 400 may define a generally wedge shaped or anatomically shaped structure, such as a structure having a sharks fin or arrowhead profile, to more closely match the surrounding anatomy of the implant site, for ease of insertion (i.e., to allow tissue distraction), and to be suitable for a tissue sparing or an oblique angular insertion approach. As can be further seen, the device 400 may have rounded edges and corners, particularly along its outer perimeter. The intermediate wall 420c may extend into convexly curved lateral walls 420a, 420b that intersect at posterolateral corners 426. The posterolateral corners 426 may be rounded, as shown, to provide overall smoothness to the implant profile and prevent undesirable damage to surrounding tissue.

The implantable interbody device 400 may include a central opening or lumen 430 extending between the upper and lower surfaces 416, 418 to facilitate bony ongrowth and bony ingrowth or fusion between adjacent bone segments, such as vertebral bodies. If so desired, the opening 430 may be used as a graft cavity to receive and hold bone graft material, or other biologically active materials like bone cement, bone void filler, bone substitute material, bone chips, demineralized bone matrix, and other similar materials. The implantable interbody device 400 may be configured in a way that optimizes the opening 430 such that the ratio of the cage or implant structure to the load bearing area is as large as possible. A graft containment porous groove may be provided within the opening 430 to contain graft material inside the graft cavity in the center of the device 400. This groove may be machined along the wall of the cavity 430 to provide additional support in keeping the graft material secured during implantation. Further, the groove may be convex, such as to serve as a boss extending into the central lumen area. This groove may be provided on any of the devices 100, 200, 300, 400 described herein.

Figure 9A:
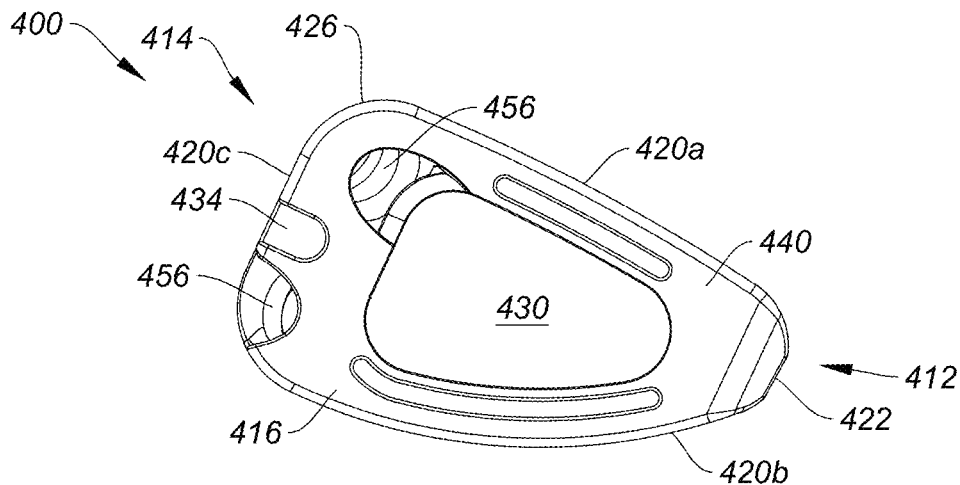
Figure 9B:
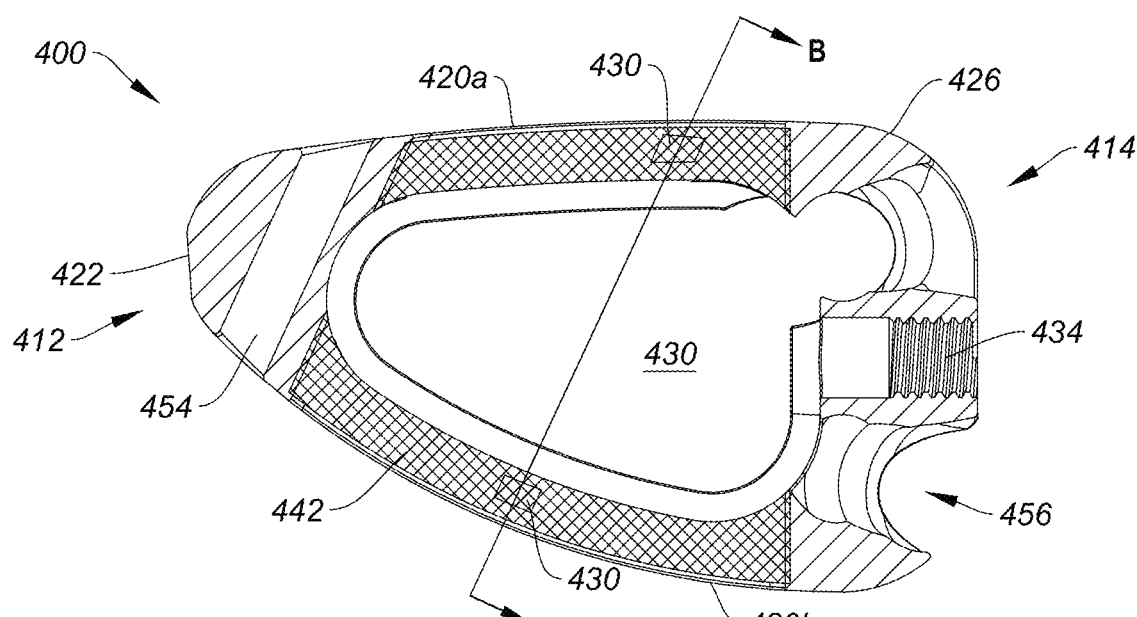
Figure 9C:
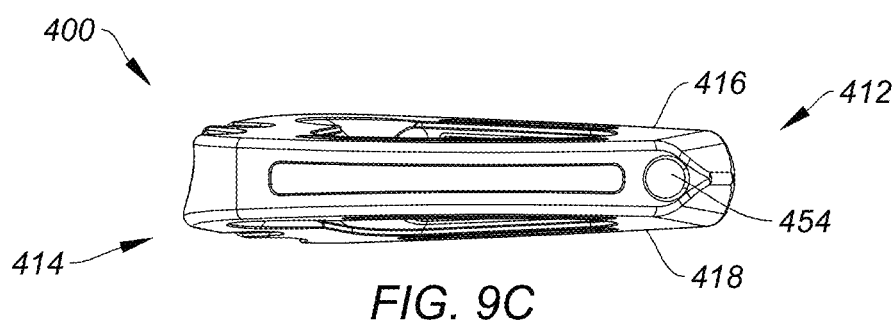
Figure 9D:
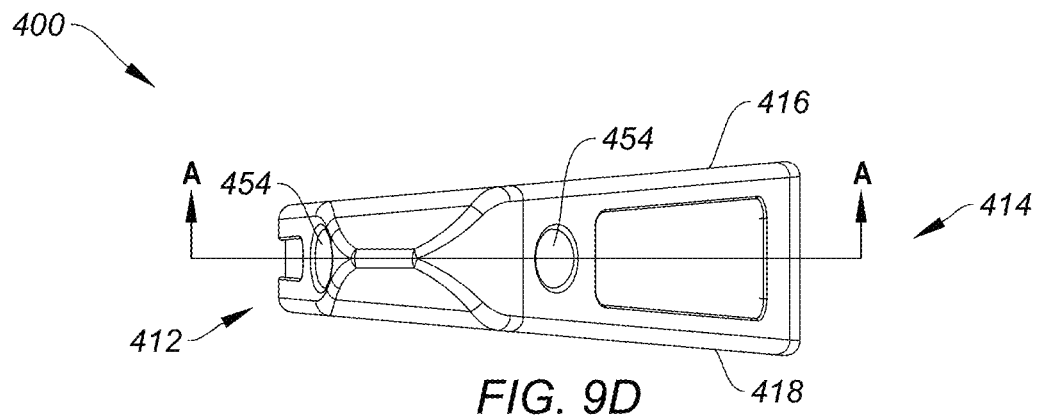

Similar to previously described devices 100, 200, 300, the implantable interbody device 400 may include bores or holes 456 to receive fixation elements such as fixation screws therethrough to secure the implantable interbody device 400 to adjacent bone tissue. Furthermore, the device 400 may include an opening 434 for receiving an insertion tool. This opening 434 may be threaded, as shown in FIG. 9B and as described above for device 100. Alternatively, the interbody device 400 may be provided without any screw holes, such as in the embodiment shown in FIGS. 10A-10E.

The screw holes 456 of this device 400, as well as the screw holes of the other previously described devices 100, 200, 300 may have a loft geometry surrounding it. Meaning, material may be removed around the screw holes 456 to facilitate screw insertion. Additionally, an indicator groove may be provided on each of the screw holes 456 to facilitate proper screw seating. This indicator groove may be a thin groove that is machined into the screw hole 456 so that it is only visible when the screw is fully seated and a split ring is engaged, for example. In one embodiment, the screw holes 456 may be configured to remain centered relative to the position of the device 400 as the height increases to allow for one introducer tool to capture the screw holes 456. In another embodiment, the screw holes 456 may be configured to translate with the endplates during use. Other optional visualization assistance features within the screw hole 456 may include etchings, colored bands, or indicator arrows. In addition, the screw holes 456 may be hourglass shaped. Similar to the screw holes described above, screw holes 456 may include a screw hole indicator groove, screw hole direction indicator arrow, a reverse chamfer or overhang feature, countersink, visual response feedback feature, and/or tactile response feedback feature, similar to the screw holes described in U.S. patent application Ser. No. 15/428,601, now U.S. Patent Application Publication No. US2017/0239061 A1, the contents of which are hereby incorporated by reference.

Without compromising stability, the lateral holes 456 may be positioned in a manner that avoids the need to retract vessels during surgery. Extended retraction of vessels during surgery may lead to greater chances for complications to the patient. Furthermore, the screw holes 456 may be closely packed and angled so that the screws converge on the oblique line.

Figure 9E:
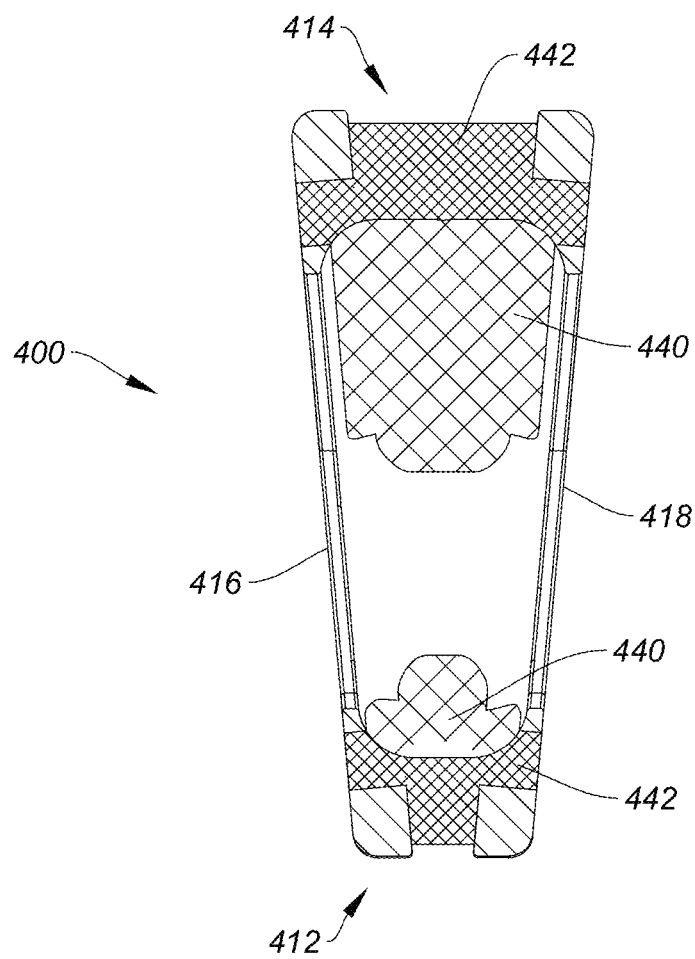

Similar to those devices 100, 200, 300 previously described, the implantable interbody device 400 may include a porous lattice or mesh component 442 within the solid scaffold structure 440 of the device 400. For instance, the implantable device 400 may have a solid structural component 440 within and on which a porous component 442 may be incorporated, as seen in FIGS. 9B and 9E, to form a combination and resultant device 400 which provides a porous component 442 within a solid structural component 440. Accordingly, the implantable interbody device 400 may incorporate the same principles of a network of pores and solid surfaces as the devices 100, 200, 300 above, to create an improved fusion facilitating device 400 for the cervical spine not heretofore seen. Since the porous component is interconnected to the solid component, greater integration is achieved than with conventional textured coatings, titanium spray coatings, or surface roughenings. These additional surface enhancements are considered optional. For instance, the solid surfaces of the device 400 may be further coated or provided with surface features like roughenings or textures. Similar to the devices 100, 200, 300 previously described, the solid scaffold structure 440 may be formed with a surface texture, and may therefore provide an outer surface that is textured, such as a roughened texture or one with discrete geometric protrusions, to enhance surface attachment.

Like devices 100, 200, 300, the extensive porous lattice areas 442 that are engineered to extend all the way around the device 400 allow for more interaction with bone than with convention enhancement methods. Such features are possible for metallic, metallic alloy or polymeric devices based on layer-by-layer deposition manufacturing techniques like 3D printing or selective layer melting (SLM) of metal, metal alloy or polymer. And since the entire device 400 may be formed of metal, metal alloy or polymer, no additional visualization markers are necessary for visualization. Because the devices 400 are created in a single process without the need for connecting subcomponents together, one of the key benefits of the devices is that the interface between the porous lattice areas 442 and the upper surface 416, lower surface 418 or sidewalls 420 is seamless and void of mechanical or chemical bonding, adding to the overall strength of the devices 400. As shown, the body of device 400 incorporates the porous lattice or mesh structures 442 into itself. The porous lattice structure 442 is not a separate panel that is added onto the body, but is integrated into the body of the device 400.

In some embodiments, the sidewalls 420*a, b, c* may be concave to create a unique C- or I-beam shape when viewed in cross-section, which serves to enhance support of the endplates and reduce risk of subsidence, while also being able to promote a lightweight, lower stiffness structure. This unique C- or I-beam cross-sectional shape of the sidewalls also helps to enhance support of any graft material contained within the central opening 424 or of biologics formed to nest within this donut shaped lumen. The sidewalls 420*a, b, c* and lumens together may be radiused in such a way to create a self-supporting arch and other geometries to reduce the need for additional supports during the manufacturing process, such as when 3D printing.

In some embodiments, the implantable interbody device 400 may have non-parallel upper and lower surfaces 416, 418 to form a wedge-shaped body. However, one skilled in the art will appreciate that the implantable interbody device 400 may also be provided with parallel upper and lower surfaces 416, 418. The implantable interbody device 400 may have any suitable shape or size to allow it to be used under lordotic or kyphotic conditions, similar to devices 100, 200, 300 above.

Similar to device 100, the device 400 may have an indicator nose through hole 454. The indicator nose through hole 454 may be configured for detection and may be used as a visual aid, such as an x-ray indicator. In addition, as shown in FIG. 9B, additional visual aids such as x-ray indicators may be present 430 in the device 400 to assist with the navigation and orientation of the device 100 during implantation. According to other aspects of the disclosure, the device 400 may include a center located "I" marker for visibility, which can be seen through the porous lattice or mesh structure 442, similar to the "I" beam 146 of device 100 which may also serve as an x-ray marker. Further, the unique hybrid scaffold structure of the device 400 enables better graft retention with its concavity. The textured exterior surface enhances bone attachment and bone fusion. As with devices 100, 200, 300 the device 400 may further include additional surface enhancements such as coatings, surface textures or surface roughenings.

It will also be appreciated that the angular positioning of the various holes, as described above, allows the present device 400 to be of a relatively small size and therefore insertable from an oblique angular approach into the intervertebral spaces of the spine. Thus, it will be appreciated that the angular positioning of the holes can assist effective operation of the device 400 and the ability to "stack" implants in adjacent multilevel procedures without the securing means interfering with each other. Such a feature can be of major significance in some situations and applications.

FIGS. 10A to 10E illustrate another exemplary embodiment of an implantable interbody device 400' configured for lateral-oblique insertion into the contra lateral and posterior space of the spine. The implantable device 400' may be implanted in the intervertebral space between vertebral bodies, without the need for additional screw fixation. Similar to device 400, the implantable interbody device 400' may be configured for insertion at an oblique angle into contra lateral and posterior space of the spine. The implantable interbody device 400' may be employed in the lumbar region of the spine. However, it is contemplated that the implantable interbody device 400' may be shaped and sized for use in other areas of the spine as well, such as the thoracic and the cervical region of the spine.

The implantable interbody device 400' may include posterior and anterior portions 412', 414', and upper and lower surfaces 416', 418' connected by two lateral walls or sidewalls 420*a'*, 420*b'* and intermediate wall segment or sidewall 420*c'*. Upper and lower surfaces 416', 418' may be flat or planar, or may be domed or convexly curved. The two lateral walls 420*a'*, 420*b'* may converge into a nose or tip 422'. This nose or tip 422' may be rounded or tapered. Collectively, the three walls 420*a'*, 420*b'*, 420*c'* may together form a generally triangular profile. However, as shown, one lateral wall 420*b'* may be greater in length than the other sidewall 420*a'*, creating a shark's fin-like shape. Additionally, the walls collectively may also form a rounded or approximately rectangular shape, particularly if one or more of the walls is curved or angled itself.

As shown, the implantable interbody device 400' may define a generally wedge shaped or anatomically shaped structure, such as a structure having a sharks fin or arrowhead profile, to more closely match the surrounding anatomy of the implant site, for ease of insertion (i.e., to allow tissue distraction), and to be suitable for a tissue sparing or an oblique angular insertion approach. As can be further seen, the device 400' may have rounded edges and corners, particularly along its outer perimeter. The intermediate wall 420c' may extend into convexly curved lateral walls 420a', 420b' that intersect at posterolateral corners 426'. The posterolateral corners 426' may be rounded, as shown, to provide overall smoothness to the implant profile and prevent undesirable damage to surrounding tissue.

The implantable interbody device 400' may include a central opening or lumen 430' extending between the upper and lower surfaces 416', 418' to facilitate bony ongrowth and bony ingrowth or fusion between adjacent bone segments, such as vertebral bodies. If so desired, the opening 430' may be used as a graft cavity to receive and hold bone graft material, or other biologically active materials like bone cement, bone void filler, bone substitute material, bone chips, demineralized bone matrix, and other similar materials. The implantable interbody device 400' may be configured in a way that optimizes the opening 430' such that the ratio of the cage or implant structure to the load bearing area is as large as possible. A graft containment porous groove may be provided within the opening 430' to contain graft material inside the graft cavity in the center of the device 400'. This groove may be machined along the wall of the cavity 430' to provide additional support in keeping the graft material secured during implantation. Further, the groove may be convex, such as to serve as a boss extending into the central lumen area. This groove may be provided on any of the devices described herein.

Figure 10A:
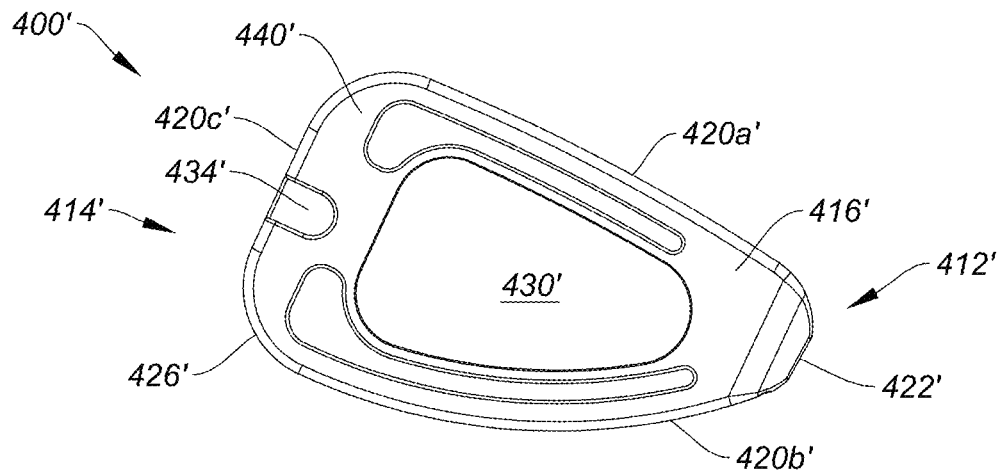
Figure 10B:
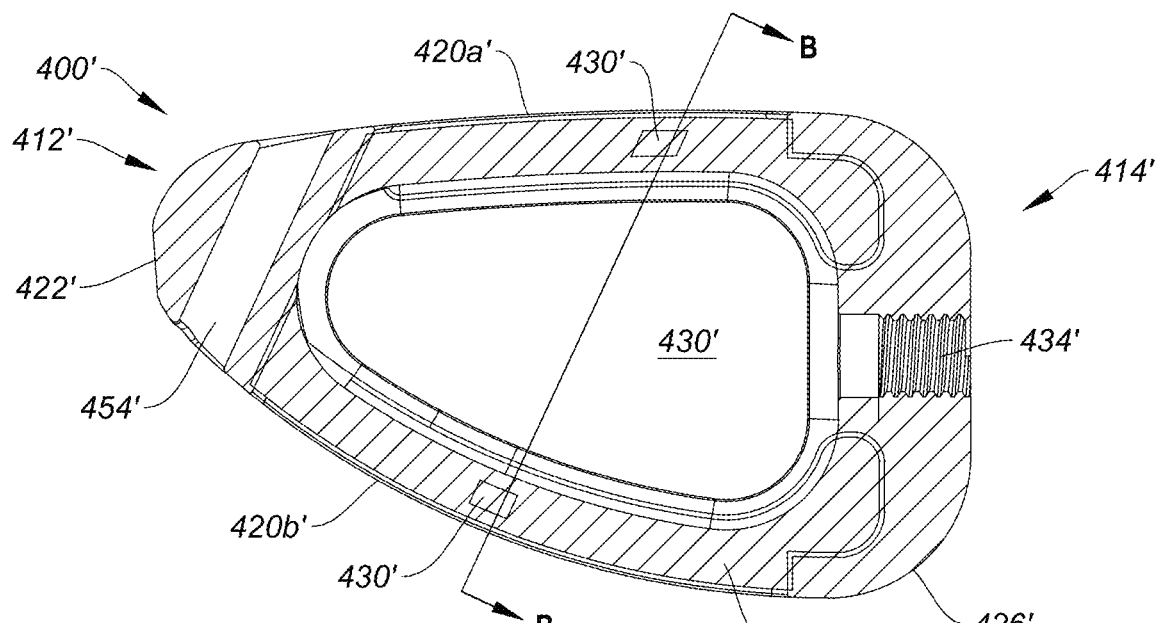
Figure 10C:
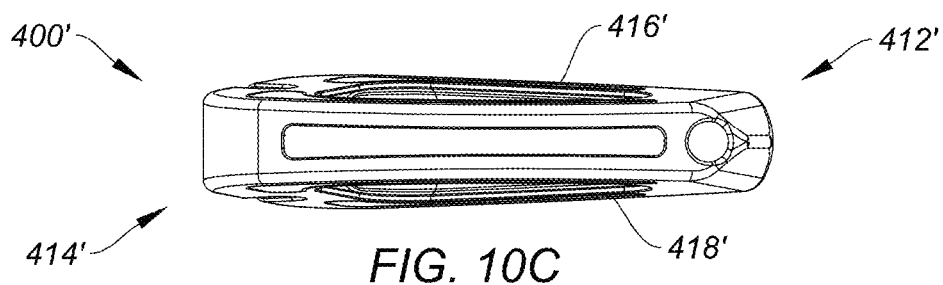
Figure 10D:
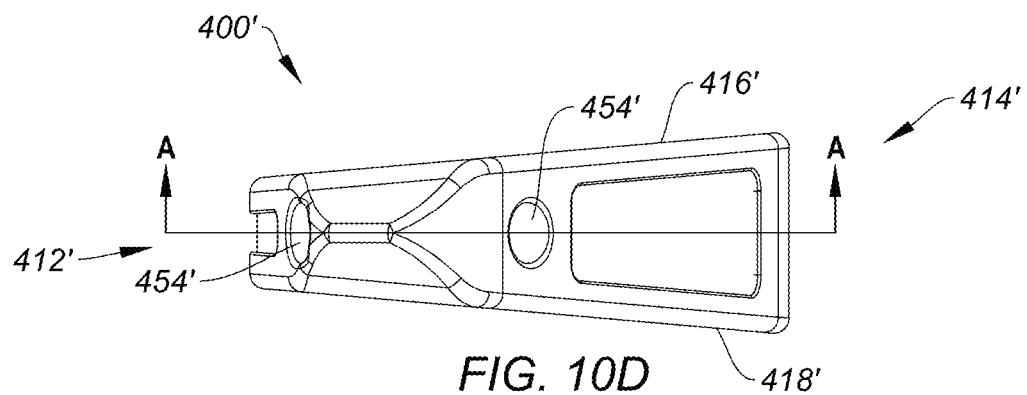
Figure 10E:
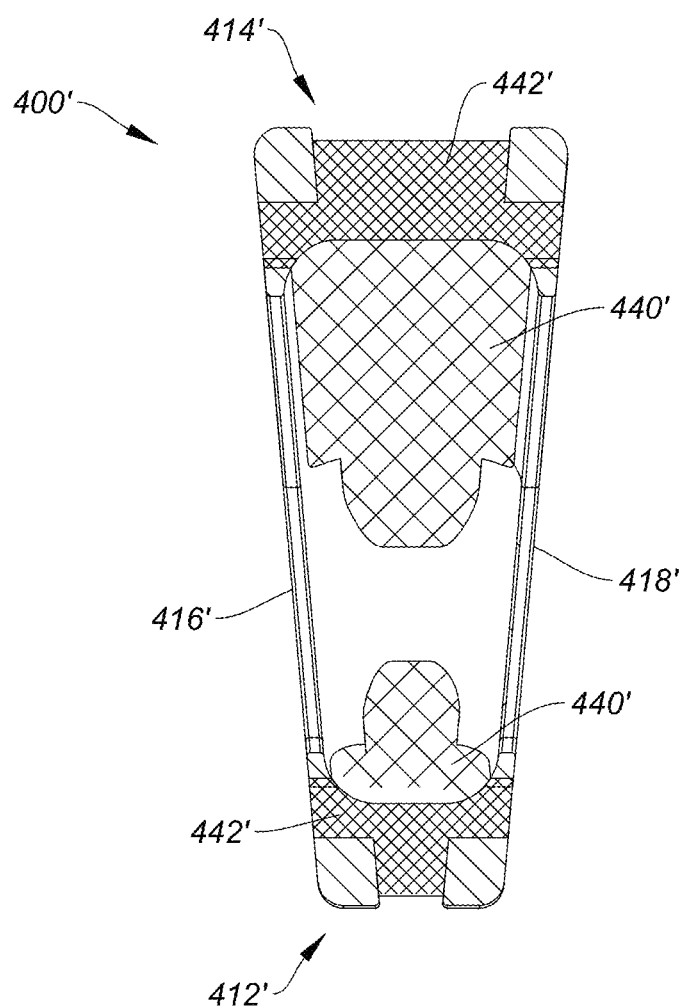

Similar to those devices 100, 200, 300 previously described, the implantable interbody device 400' may include a porous lattice or mesh component 442' within the solid scaffold structure 440' of the device 400'. For instance, the implantable device 400' may have a solid structural component 440' within and on which a porous component 442' may be incorporated, as seen in FIGS. 10B and 10E, to form a combination and resultant device 400' which provides a porous component 442 within a solid structural component 440. Accordingly, the implantable interbody device 400' may incorporate the same principles of a network of pores and solid surfaces as the devices 100, 200, 300 above, to create an improved fusion facilitating device 400' for the cervical spine not heretofore seen. Since the porous component is interconnected to the solid component, greater integration is achieved than with conventional textured coatings, titanium spray coatings, or surface roughenings. These additional surface enhancements are considered optional. For instance, the solid surfaces of the device 400' may be further coated or provided with surface features like roughenings or textures. Similar to the devices 100, 200, 300 previously described, the solid scaffold structure 440' may be formed with a surface texture, and may therefore provide an outer surface that is textured, such as a roughened texture or one with discrete geometric protrusions, to enhance surface attachment.

Like devices 100, 200, 300, the extensive porous lattice areas 442' that are engineered to extend all the way around the device 400' allow for more interaction with bone than with convention enhancement methods. Such features are possible for metallic, metallic alloy or polymeric devices based on layer-by-layer deposition manufacturing techniques like 3D printing or selective layer melting (SLM) of metal, metal alloy or polymer. And since the entire device 400' may be formed of metal, metal alloy or polymer, no additional visualization markers are necessary for visualization. Because the devices 400' are created in a single process without the need for connecting subcomponents together, one of the key benefits of the devices is that the interface between the porous lattice areas 442' and the upper surface 416', lower surface 418' or sidewalls 420' is seamless and void of mechanical or chemical bonding, adding to the overall strength of the devices 400'. As shown, the body of device 400' incorporates the porous lattice or mesh structures 442' into itself. The porous lattice structure 442' is not a separate panel that is added onto the body, but is integrated into the body of the device 400'.

Unlike implantable device 400, the implantable device 400' of the present embodiment does not include any angular screw holes at its anterior portion, or trailing end 414'. Instead, the implantable device 400' of the present embodiment may include a hole 434' as shown in FIGS. 10A-10C. The hole 434' may be threaded, as shown. The threaded hole 434' may be used for attachment of an inserter tool, or a threaded nut or screw to secure a graft component. The additional thread form enables easy oblique insertion during surgery. In addition, the threaded screw hole 434' allows for a larger graft area in the central opening 430'.

In some embodiments, the walls 420a, b, c may be concave to create a unique C- or I-beam shape when viewed in cross-section, which serves to enhance support of the endplates and reduce risk of subsidence, while also being able to promote a lightweight, lower stiffness structure. This unique C- or I-beam cross-sectional shape of the sidewalls also helps to enhance support of any graft material contained within the central opening 424' or of biologics formed to nest within this donut shaped lumen. The walls 420a, b, c and lumens together may be radiused in such a way to create a self-supporting arch and other geometries to reduce the need for additional supports during the manufacturing process, such as when 3D printing.

In some embodiments, the implantable interbody device 400' may have non-parallel upper and lower surfaces 416', 418' to form a wedge-shaped body. However, one skilled in the art will appreciate that the implantable interbody device 400 may also be provided with parallel upper and lower surfaces 416', 418'. The implantable interbody device 400' may have any suitable shape or size to allow it to be used under lordotic or kyphotic conditions, similar to devices 100, 200, 300 above.

Similar to device 400, the device 400' may have an indicator nose through hole 454'. The indicator nose through hole 454' may be configured for detection and may be used as a visual aid, such as an x-ray indicator. In addition, as shown in FIG. 10B, additional visual aids 430' such as x-ray indicators may be present 430' in the device 400 to assist with the navigation and orientation of the device 100 during implantation. According to other aspects of the disclosure, the device 400' may include a center located "I" marker for visibility, which can be seen through the porous lattice or mesh structure 442, similar to the "I" beam 146 of device 100 which may also serve as an x-ray marker. Further, the unique hybrid scaffold structure of the device 400 enables better graft retention with its concavity. The textured exterior surface enhances bone attachment and bone fusion. As with devices 100, 200, 300 the device 400' may further include additional surface enhancements such as coatings, surface textures or surface roughenings.

It will also be appreciated that the angular positioning of the various holes, as described above, allows the present device 400' to be of a relatively small size and therefore insertable from an oblique angular approach into the intervertebral spaces of the spine. Thus, it will be appreciated that the angular positioning of the holes can assist effective operation of the device 400 and the ability to "stack" implants in adjacent multilevel procedures without the securing means interfering with each other. Such a feature can be of major significance in some situations and applications.

Other embodiments of the disclosure will be apparent to those skilled in the art from consideration of the specification and practice of the disclosure provided herein. It is intended that the specification and examples be considered as exemplary only.

What is claimed is:

1. An implantable device comprising:
a generally trapezoidal shaped body configured for midline insertion between vertebral bodies of a spine, the body having an upper surface, a lower surface, an anterior portion, a posterior portion, and a pair of exterior sidewalls extending from the upper surface to the lower surface and connecting the posterior and anterior portions, the body further having openings between the upper surface and the lower surface in the exterior sidewalls,
wherein the body comprises a solid perimeter structure and a porous mesh structure contained within the solid perimeter structure, the upper surface, the lower surface and the exterior sidewalls forming the solid perimeter structure, the porous mesh structure being about 50% to about 90% porous being integrated into the solid perimeter structure and being contained within the openings of the exterior sidewalls, with the solid perimeter structure surrounding the porous mesh structure to form a single unitary structure, the porous mesh structure having a repeating geometric unit of cells, the porous mesh structure further being configured to allow bony ongrowth and bony ingrowth therethrough,
wherein an interface between the porous mesh structure and the solid perimeter structure is seamless and devoid of mechanical bonding.

2. The device of claim 1, further having a roughened, textured surface.

3. The device of claim 1, wherein the porous mesh structure comprises a plurality of randomized cell units, the porous structure further having pores between about 0.3 mm to 0.7 mm in diameter.

4. The device of claim 3, wherein each of the cell units has a dodecahedron geometry.

5. The device of claim 1, wherein the upper surface and lower surface are non-parallel such that one of the pair of sidewalls has a greater height than the other sidewall to form a wedge-shaped body.

6. The device of claim 1, wherein the device is configured to have a convex profile to nest with bony endplates.

7. The device of claim 1, further including a central opening between the upper and lower surfaces.

8. The device of claim 7, further including a porous graft containment porous groove around the central opening.

9. The device of claim 1, wherein the anterior portion of the device includes one or more apertures for receiving a fixation element.

10. The device of claim 9, wherein the one or more apertures comprises a superior aperture extending superiorly and two inferior apertures extending inferiorly.

11. The device of claim 9, wherein the one or more apertures has an hourglass shape.

12. The device of claim 1, wherein the sidewalls include an aperture for receiving an insertion tool.

13. The device of claim 1, wherein the device comprises a biocompatible metal, metal alloy or polymer.

14. The device of claim 13, wherein the biocompatible metal, metal alloy or polymer is selected from the group consisting of stainless steel, titanium, or titanium alloy.

15. The device of claim 1, wherein the vertebral bodies are cervical vertebral bodies and the body is configured for the cervical spine.

16. The device of claim 1, wherein the body includes rounded posterolateral corners.

* * * * *